(12) United States Patent
Burwell et al.

(10) Patent No.: US 10,376,711 B2
(45) Date of Patent: Aug. 13, 2019

(54) LIGHT GENERATING GUIDE WIRE FOR INTRAVASCULAR USE

(75) Inventors: Phillip Burwell, Snohomish, WA (US); Zihong Guo, Bellevue, WA (US); Jennifer K. Matson, Renton, WA (US); Steven Ross Daly, Sammamish, WA (US); David B. Shine, Sammamish, WA (US); Gary Lichttenegger, Woodinville, WA (US); Jean M. Bishop, Bothell, WA (US); Nick Yeo, Great Bookham (GB); Hugh Narciso, Santa Barbara, CA (US)

(73) Assignee: LIGHT SCIENCES ONCOLOGY INC., Bellevue, King County, WA (US)

( * ) Notice: Subject to any disclaimer, the term of this patent is extended or adjusted under 35 U.S.C. 154(b) by 2436 days.

(21) Appl. No.: 11/834,572

(22) Filed: Aug. 6, 2007

(65) Prior Publication Data

US 2008/0033519 A1 Feb. 7, 2008

Related U.S. Application Data

(63) Continuation-in-part of application No. 10/799,357, filed on Mar. 12, 2004, now Pat. No. 7,252,677.

(Continued)

(51) Int. Cl.
*A61N 1/05* (2006.01)
*A61N 5/06* (2006.01)
*A61B 18/22* (2006.01)

(52) U.S. Cl.
CPC ........... *A61N 5/062* (2013.01); *A61N 5/0601* (2013.01); *A61B 2018/2261* (2013.01);
(Continued)

(58) Field of Classification Search
CPC .............. A61N 5/0601; A61N 5/062; A61N 2005/2261; A61N 2005/0602;
(Continued)

(56) References Cited

U.S. PATENT DOCUMENTS 4,128,173 A 12/1978 Lazarus et al.
4,408,263 A 10/1983 Sternlicht
(Continued)

FOREIGN PATENT DOCUMENTS

EP 0 297 190 12/1987 .............. A61B 17/36
EP 0 755 697 A2 7/1996 ............... A61N 5/06
(Continued)

OTHER PUBLICATIONS http://www.seattleavir.com/equipsup.html.*
(Continued)

*Primary Examiner* — David Shay
(74) *Attorney, Agent, or Firm* — Troutman Sanders LLP

(57) ABSTRACT

Light sources are incorporated into a guidewire for enabling the ability to render light therapy be added to catheters that do not have that capability. In one exemplary embodiment, a solid guidewire includes a conductive core, and light sources are added to compartments formed in a distal end of the guidewire. In another exemplary embodiment, a light source array is included in a distal end of a hollow guidewire. A plurality of openings are formed into the walls of the hollow guidewire surrounding the array, enabling light to pass through the openings. Conductors extend from the array though the hollow center of the guidewire, to a proximal end of the hollow guidewire. The hollow guidewire can be coated with a conductive material, so that the coating on the guidewire serves as a conductor.

11 Claims, 12 Drawing Sheets

Related U.S. Application Data

(60) Provisional application No. 60/455,069, filed on Mar. 14, 2003.

(52) U.S. Cl.
CPC ............... *A61N 2005/0602* (2013.01); *A61N 2005/063* (2013.01); *A61N 2005/0652* (2013.01)

(58) Field of Classification Search
CPC ...... A61N 2005/063; A61N 2005/0652; A61B 2018/2261
USPC .......................... 606/7, 10–18; 607/88–93
See application file for complete search history.

(56) References Cited

U.S. PATENT DOCUMENTS

| | | |
|---|---|---|
| 4,423,725 A | 1/1984 | Baran et al. ............. 128/207.15 |
| 4,445,892 A | 5/1984 | Hussein et al. ......... 604/101.05 |
| 4,470,407 A | 9/1984 | Hussein ...................... 600/108 |
| 4,522,302 A | 6/1985 | Paikoff |
| 4,538,622 A * | 9/1985 | Samson .......... A61M 25/09033 600/434 |
| 4,545,390 A * | 10/1985 | Leary .............. A61M 25/09033 600/462 |
| 4,656,186 A | 4/1987 | Bommer et al. |
| 4,675,338 A | 6/1987 | Bommer et al. |
| 4,693,885 A | 9/1987 | Bommer et al. |
| 4,763,654 A | 8/1988 | Jang ............................ 606/195 |
| 4,773,899 A | 9/1988 | Spears ........................... 604/20 |
| 4,799,479 A | 1/1989 | Spears ........................... 606/28 |
| 4,820,349 A | 4/1989 | Saab ............................ 606/194 |
| 4,906,241 A * | 3/1990 | Noddin ................... A61L 29/06 604/103.1 |
| 4,961,738 A | 10/1990 | Mackin ......................... 606/15 |
| 4,977,177 A | 12/1990 | Bommer et al. |
| 4,983,167 A | 1/1991 | Sahota ......................... 606/194 |
| 4,997,639 A | 3/1991 | Aizawa et al. |
| 5,004,811 A | 4/1991 | Bommer et al. |
| 5,019,042 A | 5/1991 | Sahota .................... 604/101.01 |
| 5,019,075 A | 5/1991 | Spears et al. .................. 606/7 |
| 5,026,366 A | 6/1991 | Leckrone ...................... 606/7 |
| 5,034,001 A * | 7/1991 | Garrison ................... A61F 2/95 604/104 |
| 5,066,274 A | 11/1991 | Bommer et al. |
| 5,071,407 A | 12/1991 | Termin et al. ............... 604/104 |
| 5,090,958 A | 2/1992 | Sahota ...................... 604/98.01 |
| 5,104,392 A | 4/1992 | Kittrell et al. ................ 606/15 |
| 5,129,889 A | 7/1992 | Hahn et al. ................. 604/265 |
| 5,147,377 A | 9/1992 | Sahota ......................... 606/194 |
| 5,160,321 A | 11/1992 | Sahota .................... 604/101.03 |
| 5,169,395 A | 12/1992 | Narciso, Jr. ..................... 606/7 |
| 5,176,619 A | 1/1993 | Segalowitz .................... 600/18 |
| 5,178,616 A | 1/1993 | Uemiya et al. .................. 606/7 |
| 5,217,456 A | 6/1993 | Narciso, Jr. ................... 606/15 |
| 5,226,430 A | 7/1993 | Spears et al. ................ 128/898 |
| 5,267,959 A | 12/1993 | Forman ........................ 604/103 |
| 5,290,275 A | 3/1994 | Kittrell et al. ................ 606/15 |
| 5,308,861 A | 5/1994 | Aizawa et al. |
| 5,330,465 A | 7/1994 | Doiron et al. ................... 606/7 |
| 5,358,485 A | 10/1994 | Vance et al. .................. 604/22 |
| 5,370,608 A | 12/1994 | Sahota et al. .................. 604/20 |
| 5,383,467 A | 1/1995 | Auer et al. ................... 128/664 |
| 5,406,960 A | 4/1995 | Corso, Jr. ..................... 600/585 |
| 5,415,654 A | 5/1995 | Daikuzono .................... 606/15 |
| 5,417,653 A | 5/1995 | Sahota et al. .................. 604/20 |
| 5,430,051 A | 7/1995 | Aizawa et al. |
| 5,441,497 A | 8/1995 | Narciso, Jr. ................... 606/15 |
| 5,445,608 A * | 8/1995 | Chen et al. .................... 607/89 |
| 5,454,794 A | 10/1995 | Narciso, Jr. et al. ........... 607/88 |
| 5,567,409 A | 10/1996 | Aizawa et al. |
| 5,582,171 A | 12/1996 | Chornenky et al. ........ 128/653.1 |
| 5,607,419 A | 3/1997 | Amplatz et al. ................. 606/7 |
| 5,609,591 A | 3/1997 | Daikuzono .................... 606/15 |
| 5,633,275 A | 5/1997 | Mori et al. |
| 5,634,921 A | 6/1997 | Hood et al. |
| 5,662,712 A | 9/1997 | Pathak et al. .............. 623/23.64 |
| 5,700,243 A | 12/1997 | Narciso, Jr. .............. 604/102.01 |
| 5,766,234 A | 6/1998 | Chen et al. ..................... 604/92 |
| 5,766,237 A | 6/1998 | Chen et al. |
| 5,766,558 A | 6/1998 | Chen et al. ..................... 607/92 |
| 5,779,697 A | 7/1998 | Glowa et al. ................. 606/185 |
| 5,779,731 A | 7/1998 | Leavitt .......................... 606/194 |
| 5,782,896 A | 7/1998 | Chen et al. ..................... 604/88 |
| 5,800,478 A | 9/1998 | Chen et al. ..................... 607/88 |
| 5,814,008 A | 9/1998 | Chen et al. |
| 5,827,186 A | 10/1998 | Chen et al. |
| 5,830,210 A | 11/1998 | Rudko et al. .................. 606/15 |
| 5,851,221 A | 12/1998 | Rieder et al. |
| 5,865,840 A | 2/1999 | Chen |
| 5,876,426 A | 3/1999 | Kume et al. ................... 607/88 |
| 5,876,427 A | 3/1999 | Chen et al. |
| 5,947,958 A | 9/1999 | Woodard et al. .............. 606/15 |
| 5,976,106 A | 11/1999 | Verin et al. .............. 604/103.07 |
| 5,997,569 A | 12/1999 | Chen et al. |
| 5,997,571 A | 12/1999 | Farr et al. ..................... 607/92 |
| 6,013,053 A | 1/2000 | Bower et al. .............. 604/96.01 |
| 6,024,740 A | 2/2000 | Lesh et al. .................... 606/34 |
| 6,058,323 A | 5/2000 | Lemelson .................... 600/408 |
| 6,086,558 A | 7/2000 | Bower et al. .............. 604/96.01 |
| 6,096,066 A | 8/2000 | Chen et al. |
| 6,128,524 A | 10/2000 | Yoneya et al. |
| 6,146,409 A | 11/2000 | Overholt et al. .............. 606/15 |
| 6,159,236 A | 12/2000 | Biel .............................. 607/92 |
| 6,162,214 A | 12/2000 | Mueller et al. |
| 6,171,299 B1 | 1/2001 | Bonutti .......................... 606/1 |
| 6,175,669 B1 | 1/2001 | Colston et al. ................ 385/12 |
| 6,193,676 B1 | 2/2001 | Winston et al. ............. 600/585 |
| 6,210,425 B1 | 4/2001 | Chen |
| RE37,180 E | 5/2001 | Mori et al. |
| 6,231,568 B1 | 5/2001 | Loeb et al. .................... 606/15 |
| 6,238,426 B1 | 5/2001 | Chen |
| 6,240,925 B1 | 6/2001 | McMillan et al. |
| 6,245,012 B1 | 6/2001 | Kleshinski ................... 623/1.11 |
| 6,254,571 B1 | 7/2001 | Hart ............................. 604/107 |
| 6,254,599 B1 | 7/2001 | Lesh et al. .................... 606/41 |
| 6,273,904 B1 | 8/2001 | Chen et al. |
| 6,290,668 B1 | 9/2001 | Gregory et al. ................ 604/22 |
| 6,299,599 B1 | 10/2001 | Pham et al. .................. 604/113 |
| 6,319,273 B1 | 11/2001 | Chen et al. |
| 6,336,934 B1 | 1/2002 | Gilson et al. ................ 606/200 |
| 6,344,050 B1 | 2/2002 | Chen |
| 6,350,772 B1 | 2/2002 | Kuroiwa et al. |
| 6,355,030 B1 | 3/2002 | Aldrich et al. ................ 606/28 |
| 6,413,495 B1 | 7/2002 | Aizawa et al. |
| 6,416,511 B1 | 7/2002 | Lesh et al. .................... 606/41 |
| 6,416,531 B2 | 7/2002 | Chen |
| 6,445,011 B1 | 9/2002 | Hirano et al. |
| 6,454,789 B1 | 9/2002 | Chen et al. |
| 6,468,244 B1 | 10/2002 | Leone et al. .............. 604/103.02 |
| 6,485,502 B2 | 11/2002 | Don Michael et al. ....... 606/200 |
| 6,496,737 B2 | 12/2002 | Rudie et al. .................. 607/101 |
| 6,508,784 B1 | 1/2003 | Shu ........................... 604/96.01 |
| 6,540,767 B1 | 4/2003 | Walak et al. ................. 606/200 |
| 6,562,031 B2 | 5/2003 | Chandrasekaran et al. ..... 606/41 |
| 6,562,058 B2 | 5/2003 | Seguin et al. ................ 606/200 |
| 6,575,965 B1 | 6/2003 | Fitch et al. .................... 606/15 |
| 6,575,966 B2 | 6/2003 | Lane et al. .................... 606/21 |
| 6,585,655 B2 | 7/2003 | Crowley ...................... 600/463 |
| 6,602,274 B1 | 8/2003 | Chen |
| 6,605,030 B2 | 8/2003 | Weinberger ..................... 600/3 |
| 6,616,629 B1 | 9/2003 | Verin et al. .............. 604/101.05 |
| 6,634,765 B2 | 10/2003 | Lin .............................. 362/249 |
| 6,653,337 B2 | 11/2003 | Kuroiwa et al. |
| 6,656,174 B1 | 12/2003 | Hegde et al. .................. 606/41 |
| 6,661,167 B2 | 12/2003 | Eliashevich et al. |
| 6,689,380 B1 | 2/2004 | Marchitto et al. |
| 6,749,623 B1 | 6/2004 | Hsi et al. ....................... 607/88 |
| 6,784,460 B2 | 8/2004 | Ng et al. |
| 6,811,562 B1 | 11/2004 | Pless ............................ 607/88 |
| 6,830,584 B1 | 12/2004 | Seguin ......................... 623/2.11 |
| 6,872,205 B2 | 3/2005 | Lesh et al. .................... 606/41 |
| 6,899,723 B2 | 5/2005 | Chen |
| 6,953,457 B2 | 10/2005 | Farr et al. ..................... 606/15 |

(56) References Cited

U.S. PATENT DOCUMENTS

| | | | |
|---|---|---|---|
| 6,958,498 B2 | 10/2005 | Shelton et al. | |
| 6,962,584 B1 | 10/2005 | Stone et al. | 606/7 |
| 6,984,655 B1 | 1/2006 | Mori et al. | |
| 6,986,782 B2 | 1/2006 | Chen et al. | |
| 7,015,240 B2 | 3/2006 | North et al. | |
| 7,018,395 B2 | 3/2006 | Chen | |
| RE39,357 E | 10/2006 | Yoneya et al. | |
| 7,252,677 B2 | 8/2007 | Burwell et al. | |
| 7,396,354 B2 | 7/2008 | Rychnovsky | 606/15 |
| 7,405,208 B2 | 7/2008 | Santi et al. | |
| 7,498,029 B2 | 3/2009 | Hasan et al. | |
| 7,667,039 B2 | 2/2010 | Garcia-Echeverria et al. | |
| 7,730,894 B2 | 6/2010 | Burwell et al. | |
| 7,943,562 B2 | 5/2011 | Lee et al. | |
| 7,993,640 B2 | 8/2011 | Chen | |
| 2001/0029337 A1 | 10/2001 | Pantages et al. | 600/463 |
| 2001/0049502 A1 | 12/2001 | Chen | |
| 2002/0004053 A1 | 1/2002 | Biel | |
| 2002/0127224 A1 | 9/2002 | Chen | |
| 2002/0127230 A1 | 9/2002 | Chen | |
| 2003/0018371 A1 | 1/2003 | Chen | |
| 2003/0109813 A1 | 6/2003 | Chen | |
| 2003/0114434 A1 | 6/2003 | Chen et al. | |
| 2003/0114744 A1 | 6/2003 | Pantages et al. | 600/407 |
| 2003/0167033 A1 | 9/2003 | Chen et al. | |
| 2003/0195495 A1 | 10/2003 | Ryan et al. | 606/15 |
| 2003/0208249 A1 | 11/2003 | Chen | |
| 2004/0122419 A1 | 6/2004 | Neuberger | |
| 2005/0004510 A1 | 1/2005 | Chen | |
| 2005/0013812 A1 | 1/2005 | Dow et al. | |
| 2005/0038419 A9 | 2/2005 | Arnold et al. | 606/15 |
| 2005/0085455 A1 | 4/2005 | Chen | |
| 2005/0113815 A1 | 5/2005 | Ritchie et al. | |
| 2005/0131510 A1 | 6/2005 | Chen et al. | |
| 2005/0187597 A1 | 8/2005 | Vanderschuit | |
| 2005/0196401 A1 | 9/2005 | Chen | |
| 2005/0197534 A1 | 9/2005 | Barbato et al. | 600/173 |
| 2005/0228260 A1 | 10/2005 | Burwell et al. | |
| 2005/0251131 A1 | 10/2005 | Lesh | 606/41 |
| 2005/0279354 A1 | 12/2005 | Deutsch et al. | |
| 2006/0067889 A1 | 3/2006 | Pallenberg et al. | |
| 2006/0155348 A1* | 7/2006 | deCharms | A61N 5/0601 607/89 |
| 2006/0211639 A1 | 9/2006 | Bratzler et al. | |
| 2006/0265031 A1 | 11/2006 | Skwarek et al. | |
| 2006/0282132 A1 | 12/2006 | Arai et al. | |
| 2007/0002582 A1* | 1/2007 | Burwell | A61N 5/062 362/572 |
| 2007/0010782 A1 | 1/2007 | Doty et al. | 604/20 |
| 2007/0038204 A1 | 2/2007 | Chen et al. | 606/17 |
| 2007/0059316 A1 | 3/2007 | Pallenberg et al. | |
| 2007/0129776 A1 | 6/2007 | Robins et al. | |
| 2007/0142880 A1 | 6/2007 | Barnard et al. | |
| 2008/0269846 A1 | 10/2008 | Burwell et al. | |
| 2009/0163982 A1* | 6/2009 | deCharms | A61N 5/0601 607/89 |
| 2010/0274330 A1 | 10/2010 | Burwell et al. | |
| 2011/0008372 A1 | 1/2011 | Chen | |
| 2011/0236402 A1 | 9/2011 | Chen | |
| 2012/0179228 A1* | 7/2012 | DeCharms | A61N 5/0601 607/89 |
| 2013/0231721 A1* | 9/2013 | DeCharms | A61N 5/0601 607/89 |

FOREIGN PATENT DOCUMENTS

| | | | |
|---|---|---|---|
| EP | 0 820 786 | 1/1998 | A61N 5/06 |
| EP | 1610865 | 1/2006 | |
| JP | 02-185269 | 7/1990 | A61N 5/06 |
| JP | 07-095986 | 4/1995 | A61B 17/36 |
| JP | 2001-129094 | 5/2001 | A61M 25/00 |
| WO | WO 96/00527 | 1/1996 | A61B 17/36 |
| WO | WO 96/29943 | 10/1996 | A61B 17/22 |
| WO | WO 97/32520 | 9/1997 | A61B 5/04 |
| WO | WO9822184 * | 5/1998 | 606/10 |
| WO | WO 98/32493 | 7/1998 | A61N 5/06 |
| WO | WO 01/89598 | 11/2001 | |
| WO | WO 02/07629 | 1/2002 | A61B 18/18 |
| WO | WO-2002024199 A1 | 3/2002 | |
| WO | WO-2003074566 A2 | 9/2003 | |
| WO | WO 04/82736 | 9/2004 | |
| WO | WO-2006036968 A2 | 4/2006 | |

OTHER PUBLICATIONS http://dictionary.reference.com/browse/additive.*
http://www.merriam-webster.com/dictionary/encapsulate.*
PCT International Search Report, PCT Patent Application PCT/US2004/007563, dated Sep. 2, 2005, 1 page.
International Searching Authority, Written Opinion, PCT Patent Application PCT/US2004/007563, dated Sep. 2, 2005, 3 pages.
PCT International Preliminary Examination Report, PCT Patent Application PCT/US2004/007563, dated Mar. 20, 2006, 3 pages.
European Patent Office, Supplementary Partial European Search Report, EP Patent Application 04720378.1, dated Oct. 26, 2007, 5 pages.
European Patent Office, Examination Report, EP Patent Application 04720378.1, dated Apr. 27, 2010, 5 pages.
European Patent Office, Examination Report, EP Patent Application 04720378.1, dated Feb. 17, 2012, 4 pages.
Anichini et al., "The paradox of T cell-mediated antitumor immunity in spite of poor clinical outcome in human melanoma," *Cancer Immunol Immunother*, vol. 53: 855-864, 2004.
Armeanu et al., "Direct and Natural Killer Cell-Mediated Antitumor Effects of Low-Dose Bortezomib in Hepatocellular Carcinoma," *Clin Cancer Res*, vol. 14, No. 11: 3520-3528, 2008.
Bae et al., "Photodynamic therapy-generated tumor celllysates with CpG-ogliodeoxynucleotide enhance immunotherapy efficacy in human papillomavirus 16 (E6/E7) immortalized tumor cells," *Cancer Science*, vol. 98, No. 5: 747-752, 2007.
Baecher-Allan et al., "Immune regulation in tumor-bearing hosts," *Current Opinion in Immunology*, vol. 18: 214-219, 2006.
Benigni et al., "Phenotype and Homing of CD4 Tumor-Specific T Cells is Modulated by Tumor Bulk," *The Journal of Immunology*, vol. 175: 739-748, 2005.
Bromley et al., "Characterization of an antitumor immune response after light-activated drug therapy using talaporfin sodium in a spontaneously metastasizing mammary tumor model," ASCO Meeting Abstracts: 2pp, 2009.
Bunt et al., "Tumor-Associated Myeloid-Derived Suppressor Cells," *Cancer Immunotherapy*, Chapter 17: 309-331, 2007.
Campoli et al., "Tumor-Induced Immune Suppression and Immune Escape," Cancer Drug Discovery and Development: Immunotherapy of Cancer, Ch. 15: 263-284, 2006.
Canti et al., "Photodynamic therapy and the immune system in experimental oncology." *Photochem. Photobiol. Sci.* vol. 1: 79-80, 2002.
Castano et al., "Specific anti-tumor immune response with photodynamic therapy mediated by benzoporphyrin derivative and chlorine (e6)," Proceedings of SPIE, vol. 4961: 1-9, 2003.
Chen et al., "New Technology for Deep Light Distribution in Tissue for Phototherapy," *Cancer J*, vol. 8: 154-163, 2002.
Coukos et al., "The Tumor Microenvironment," Cancer Drug Discovery and Development: *Immunotherapy of Cancer*, Ch. 16: 285-301, 2006.
Danna et al., "Surgical Removal of Primary Tumor Reverses Tumor-Induced Immunosuppression Despite the Presence of Metastatic Disease," *Cancer Research*, vol. 64: 2205-2211, 2004.
Das et al., "Induction of apoptosis and manganese superoxide dismutase gene by photodynamic therapy in cervical carcinoma cell lines," *Int J Clin. Oncol*, vol. 5:97-103, 2000.
De Visser et al., "Effects of TGF-? on the immune system: implications for cancer immunotherapy," *Leukemia*, vol. 13: 1188-1199, 1999.
De Visser, Karin, "Spontaneous immune responses to sporadic tumors: tumor-promoting, tumor-protective or both?" *Cancer Immunol Immunother* vol. 57: 1531-1539, 2008.

(56) References Cited

OTHER PUBLICATIONS

Derhovanessian et al., "Immunity, ageing, and cancer," *Immunity & Ageing*, vol. 5: 16pp, 2008.
Disis et al., "Use of tumour-responsive T cells as cancer treatment," www.thelancet.com. vol. 373: 674-683, 2009.
Emens et al., "Manipulating Immunological Checkpoints to Maximize Antitumor Immunity," Cancer Drug Discovery and Development: Immunotherapy of Cancer, Ch. 19: 331-353, 2006.
Engel et al., "A Phase II Study of Single Agent Bortezomib in Patients with Metastatic Breast Cancer: A Single Institution Experience," *Cancer Investigation*, vol. 25, No. 8: 733-737, 2007.
Finn, Olivera., "Cancer Immunology," *N Engl. J Med*, vol. 358, No. 25: 2704-2715, Jun. 19, 2008.
Fong et al., "Anti-Cytotoxic T-Lymphocyte Antigen-4 Antibody: The First in an Emerging Class of Immunomodulatory Antibodies for Cancer Treatment," *Journal of Clinical Oncology*, vol. 26, No. 32: 5275-5283, 2008.
Frumento et al., "Targeting Tumor-Related Immunosuppression for Cancer Immunotherapy," Endocrine, Metabolic, & Immune Disorders—*Drug Targets*, vol. 6: 223-237, 2006.
Gajewski et al., "Immune resistance orchestrated by the tumor microenvironment," *Immunological Reviews*, vol. 213: 131-145, 2006.
Gajewski et al., "Immune suppression in the Tumor Microenvironment," *J Immunother*, vol. 29, No. 3: 233-240, 2006.
Ganss et al., "Overcoming tumor-intrinsic resistance to immune effector function," *Eur. J Immunol.*, vol. 34: 2635-2641, 2004.
Goldszmid et al., "Dendritic Cells Charged with Apoptotic Tumor Cells Induce Long-Lived Protective CD4+ and CD8+ T Cell Immunity against B16 Melonoma," *The Journal of Immunology*: 5940-5947, 2003.
Gollnick et al., "Generation of Effective Antitumor Vaccines Using Photodynamic Therapy," *Cancer Research*, vol. 62: 1604-1608, 2002.
Gollnick et al., "Photodynamic Therapy and Anti-Tumor Immunity," *Lasers in Surgery and Medicine*, vol. 38: 509-515, 2006.
Gollnick et al., "Photodynamic therapy (PDT) control of distant disease through immune mechanisms," *Proc Amer Assoc Cancer Res*, vol. 45: 2pp, 2004.
Gonzalez et al., "Effect of surgical resection of metastatic disease on immune tolerance to cancer. How a systemic disease could be controlled by a local therapy," *Clin Transl Oncol*, vol. 9: 571-577, 2007.
Gravekamp et al., "Cancer vaccination: Manipulation of immune responses at old age," *Mechanisms of Ageing and Development*, vol. 130: 67-75, 2009.
Gupta, Sudhir, "Molecular mechanisms of apoptosis in the cells of the immune system in human aging," *Immunological Reviews* vol. 205: 114-129, 2005.
Halliday et al., "Spontaneous Regression of Human Melanoma/Nonmelanoma Skin Cancer: Association with Infiltrating CD4+ T Cells," *World J Surg.*, vol. 19: 352-358, 1995.
Hamblin et al., "Combination Immunotherapy and Photodynamic Therapy for Cancer," Proceedings of SPIE, vol. 6087: 12pp, 2006.
Hamblin et al., "Scavenger receptor-targeted photodynamic therapy of 1774 tumors in mice: tumor response and concomitant immunity," Proceedings of SPIE, vol. 4617: 1-10, 2002.
Harvey et al., "Killing tumor cells: the effect of photodynamic therapy using mono-L-aspartyl chlorine and NS-398," *The American Journal of Surgery*, vol. 189: 302-305, 2005.
Henderson et al., "Choice of Oxygen-Conserving Treatment Regimen Determines the Inflammatory Response and Outcome of Photodynamic Therapy of Tumors," *Cancer Research*, vol. 64: 2120-2126, 2004.
Igney et al., "Immune escape of tumors: apoptosis resistance and tumor counterattack," *Journal of Leukocyte Biology*, vol. 71: 907-920, Jun. 2002.
Ishikawa et al., "Perioperative immune responses in cancer patients undergoing digestive surgeries," *World Journal of Surgical Oncology*, vol. 7, No. 7: 22pp, 2009.

Ito, Takashi, "Cellular and Subcellular Mechanisms of Photodynamic Action: The 102 Hypothesis as a Driving Force in Recent Research," *Photochemistry and Photobiology*. vol. 28: 493-508, 1978.
Jackaman et al., "Deliberately provoking local inflammation drives tumors to become their own protective vaccine site," *International Immunology*, vol. 20, No. 11: 1467-1479, 2008.
Kabingu et al., "CD8+ T cell-mediated control of distant tumours following local photodynamic therapy is independent of CD4+ T cells and dependent on natural killer cells," *British Journal of Cancer*. 1-10, 2007.
Kaufman et al., "Immune system versus tumor: shifting the balance in favor of DCs and effective immunity," *The Journal of Clinical Investigation*, vol. 113, No. 5: 664-667, 2004.
Kessel et al., "Mitochondrial photo damage and PDT-induced apoptosis," *Journal of Photochemistry and Photobiology B*, vol. 42: 89-95, 1998.
Kim et al., "Cancer Cell Immune Escape and Tumor Progression by Exploitation of Anti-Inflammatory and Pro-Inflammatory Responses," *Cancer Biology and Therapy*, vol. 4, No. 9: 924-933, 2005.
Kim et al., "Tumor-Driven Evolution of Immunosuppressive Networks during Malignant Progression," *Cancer Res*, vol. 66, No. 11: 5527-5536, 2006.
Klebanoff et al., "CD8+ T-cell memory in tumor immunology and immunotherapy," *Immunol. Rev.*, vol. 211: 214-224, 2006.
Korbelik, Mladen., "Advances in the understanding of host response associated with tumor PDT," Biophotonics and Immune Responses II, Proc. of SPIE, vol. 6438: 10pp., 2007.
Korbelik et al., "Interaction Between Photodynamic Therapy and BCG Immunotherapy Responsible for the Reduced Recurrence of Treated Mouse Tumors," *Photochemistry and Photobiology*, vol. 73, No. 4: 403-409, 2001.
Korbelik et al., "Photodynamic therapy-generated vaccine for cancer therapy," *Cancer Immunol. Immunother.*, vol. 55: 900-909, 2006.
Korbelik et al., "Photodynamic therapy-generated vaccines: relevance of tumour cell death expression," *British Journal of Cancer*. 1-7, 2007.
Korbelik et al., "Photodynamic Therapy-Induced Cell Surface Expression and Release of Heat Shock Proteins: Relevance for Tumor Response," *Cancer Res.*, vol. 65, No. 3: 1018-1026, 2005.
Korbelik et al., "Photodynamic Therapy-mediated Immune Response against Subcutaneous Mouse Tumors," *Cancer Research*, vol. 59: 1941-1946, 1999.
Kujundzic et al., "A Phase II Safety and Effect on Time to Tumor Progression Study of Intratumoral Light Infusion Technology Using Talaporfin Sodium in Patients With Metastatic Colorectal Cancer," *Journal of Surgical Oncology*: 1-7, 2007.
Lehrnbecher et al., "Changes in host defence induced by malignancies and antineoplastic treatment: implication for immunotherapeutic strategies," *Lancet Oncology*, vol. 9: 269-278, 2008.
Li et al., "Apoptosis and expression of cytokines triggered by pyropheophorbide-a methyl ester-mediated photodynamic therapy in nasopharyngeal carcinoma cells," *Photodiagnosis and Photodynamic Therapy*, vol. 3: 247-258, 2006.
Liu et al., "Overcoming Immune Tolerance to Cancer by Heat Shock Protein Vaccines," *Molecular Cancer Therapeutics*, vol. 1: 1147-1151, 2002.
Lustgarten, Joseph, "Cancer, aging and immunotherapy: lessons learned from animal models," *Cancer Immunol. Immunother.*: 11pp., 2009.
Lustig et al., "A Multicenter Phase I Safety Study of Intratumoral Photo activation of Talaporfin Sodium in Patients with Refractory Solid Tumors," *Cancer*, vol. 98, No. 8: 1767-1771, 2003.
Mohebtash et al., "Phase I trial of PSA-TRICOM vaccine and ipilimumab in patients (Pts) with metastatic castrate-resistant prostrate cancer (mCRPC)," Genitourinary Cancers Symposium: Abstract only 3pp, 2009.
Molhoek et al., "Apoptosis of CD4+CD25high T cells in response to Sirolimus requires activation of T cell receptor and is modulated by IL-2," *Cancer Immunol Immunother.*, vol. 58: 867-876, 2009.
Morton et al., "Cytoreductive Surgery and Adjuvant Immunotherapy: A New Management Paradigm for Metastatic Melanoma," *CA Cancer J Clin*, vol. 49, No. 2: 101-116, 1999.

(56) References Cited

OTHER PUBLICATIONS

Mozaffari et al., "NK-cell and T-cell functions in patients with breast cancer: effects of surgery and adjuvant chemo- and radiotherapy," *British Journal of Cancer*, vol. 97: 105-111, 2007.

Myrianthefs et al., "Cancer cachexia and immunomodulation," *Journal of BUON*, vol. 10: 181-188, 2005.

Nigam et al., "Immunomodulatory properties of antineoplastic drugs administered in conjunction with GM-CSF-secreting cancer cell vaccines," *International Journal of Oncology*, vol. 12: 161-170, 1998.

Nowis et al., "The influence of photodynamic therapy on the immune response," *Photodiagnosis and Photodynamic Therapy*, vol. 2: 283-298, 2005.

Nylandsted et al., "Selective depletion of heat shock protein 70 (Hsp70) activates a tumor-specific death program that is independent of caspases and bypasses Bcl-2," *PNAS*, vol. 97, No. 14: 7871-7876, 2000.

Ochsenbein, Adrian, "Principles of tumor immunosurveillance and implications for immunotherapy," *Cancer Gene Therapy*, vol. 9: 1043-1055, 2002.

Oseroff, Alan, "PDT as a Cytotoxic Agent and Biological Response Modifier: Implications for Cancer Prevention and Treatment in Immunosuppressed and Immunocompetent Patients," *Journal of Investigative Dermatology*, vol. 126: 542-544, 2006.

Pilling et al., "Prolonged Survival Due to Spontaneous Regression and Surgical Excision of Malignant Mesothelioma," *The Society of Thoracic Surgeons*, vol. 83: 314-315, 2007.

Pockley, A. Graham., "Heat shock proteins as regulators of the immune response," *The Lancet*, vol. 362: 469-476, 2003.

Preise et al., "Systemic antitumor protection by vascular-targeted photodynamic therapy involves cellular and humoral immunity," *Cancer Immunol. Immunother.*, vol. 58: 71-84, 2009.

Prendergast, George, "Breaking Immune Suppression in Cancer: The Emerging Revolution in Immunotherapy." *Cancer Reviews Online*, vol. 7: 13-14, 2007.

Printz, Carrie, "Spontaneous Regression of Melanoma May Offer Insight Into Cancer Immunology," *JNCI Journal of the National Cancer Institute*, vol. 93, No. 14: 1047-1048, 2001.

Rabinovich et al., "Programmed Death Ligand-I and Galectin-I: Pieces in the Puzzle of Tumor-Immune Escape," *Cancer Immunotherapy*, Chapter 18: 333-346, 2007.

Salazar et al., "Cancer Vaccines: The Role of Tumor Burden in Tipping the Scale Towards Vaccine Efficacy," *Journal of Clinical Oncology*, vol. 23, No. 30: 7397-7398, 2005.

Schmid et al., "A phase IIII study of bortezomib and capecitabine in patients with metastatic breast cancer previously treated with taxanes and/or anthracyclines," *Annals of Oncology*, vol. 19: 871-876, 2008.

Schumacher et al., "Immunosensitization of Tumor Cells to Dendritic Cell Activated Immune Responses with the Proteasome Inhibitor Bortezomib (PS-341, Velcade)," *The Journal of Immunology*, vol. 176: 4757-4765, 2006.

Smyth et al., "CD4+CD25+ T Regulatory Cells Suppress NK Cell-Mediated Immunotherapy of Cancer," *The Journal of Immunology*, vol. 176: 1582-1587, 2006.

Spiesek et al., "Bortezomib enhances dendritic cell (DC)-mediated induction of immunity to human myeloma via exposure of cell surface heat shock protein 90 on dying tumor cells: therapeutic implications," *Immunobiology*, vol. 109, No. 11: 4839-4845, 2007.

Staal et al., "The Marriage of Growth Factor Inhibitors and Chemotherapy: Bliss or Bust?" *Journal of Clinical Oncology*, vol. 27, No. 10: 1545-1548, 2009.

Stewart et al., "Altered Immune Function during Long-Term Host-Tumor Interactions Can Be Modulated to Retard Autochthonous Neoplastic Growth," *The Journal of Immunology*: 2851-2859, 2007.

Stewart et al., "Immunological responses can have both pro-and antitumour effects: implications for immunotherapy," *Expert Reviews in Molecular Medicine*, vol. 9, Issue 4: 1-20, 2007.

Stoll, Basil A., "Spontaneous regression of cancer: new insights," *Biotherapy*, vol. 4: 23-30, 1992.

Tapia et al., "Activity of bortezomib, a proteasome inhibitor, in breast cancer cells: association with negative estrogen receptor and IKKINF-?B expression," *ASCO Annual Meeting Abstracts*: 3pp., 2005.

Thirumaran et al., "Cytotoxic Chemotherapy in Clinical Treatment of Cancer," *Cancer Immunotherapy*, Chapter 7: 101-116, 2007.

Thong et al., "Immune Response Against Angiosarcoma Following Lower Fluence Rate Clinical Photodynamic Therapy," *Journal of Environmental Pathology, Toxicology, and Oncology*, vol. 27, No. 1: 43-50, 2008.

Thong et al., "Photodynamic-therapy-activated immune response against distant untreated tumours in recurrent angiosarcoma,." *Lancet Oncology*, vol. 8: 950-952, 2007.

Valenti et al., "Tumor-Released Microvesicles as Vehicles of Immunosuppression," *Cancer Res.*, vol. 67, No. 7: 2912-2915, 2007.

Van Duijnhoven et al., "The immunological consequences of photodynamic treatment of cancer, a literature review." *Immunobiology*, vol. 207: 105-113, 2003.

Waldmann, Thomas, "Effective Cancer Therapy Through Immunomodulation," *Annu. Rev. Med.*, vol. 57: 65-81, 2006.

Wang et al., "A phase IIII safety and efficacy study of intra tumoral light-activated drug therapy using talaporfin sodium in patients with inoperable hepatocellular carcinoma," ANSO Annual Meeting Abstracts: 2pp, 2009.

Wang, Rong-fu., "Regulatory T Cells in Tumor Immunity: Role of Toll-Like Receptors," *Cancer Immunotherapy*, Chapter 15: 277-287, 2007.

Whiteside, Theresa, "The Role of Immune Cells in the Tumor Microenvironment," *Cancer Treatment and Research*, vol. 130, Chapter 5: 103-124, 2006.

Widen et al., "Overcoming immunosuppressive mechanisms," *Annals of Oncology*, vol. 19, Supplement 7: vii241-vii247, 2008.

Wojtowicz-Praga, Slawomir., "Reversal of Tumor-Induced Immunosuppression: A New Approach to Cancer Therapy," *Journal of Immunotherapy*, vol. 20, No. 3: 165-177, 1997.

Yakirevich et al., "Regulatory T Lymphocytes: Pivotal Components of the Host Antitumor Response," *Journal of Clinical Oncology*, vol. 25, No. 18: 2506-2508, 2007.

Yang et al., "Bortezomib (VEL CAD E) in metastatic breast cancer: pharmacodynamics, biological effects, and prediction of clinical benefits," *Annals of Oncology*, vol. 17: 813-817, 2006.

Yu et al., "Priming of naïve T cells inside tumors leads to eradication of established tumors," *Nature Immunology*, vol. 5, No. 2: 141-149, 2004.

Zhang et al., "Generation of effective vaccines against liver cancer by using photodynamic therapy," *Lasers Med Sci*: 4pp., 2008.

Zwierzina, H., "Combining immunotherapy with classical anticancer therapy," *Annals of Oncology*, vol. 19, Supplement 7: vii252-vii255, 2008.

Unknown, "A Phase 3 Study of Talaporfin Sodium and Interstitial Light Emitting Diodes Treating Hepatocellular Carcinoma (HCC)," Study NCT00355355. 4pp., 2009.

Unknown, "Phase 3 Trial of LitxTM Plus Chemotherapy vs. Chemotherapy Only Treating Coloretal Cancer Patients With Recurrent Liver Metastatases," Study NCT00440310. 4pp., 2009.

Decker, Christine. "OSHU Cancer Institute Finds That Drug Stimulated Immune System in Prostate Cancer. *Medical News Today*," Jun. 4, 2008, 3 pp. <http://www.medicalnewstoday.com/articles/109743.php>.

Wolchok et al. "The Mechanism of Anti-CTLA-4 Activity and the Negative Regulation of T-Cell Activation." *The Oncologist*, vol. 13, Oct. 2008, 9 pp. http://theoncologist.alphamedpress.org/cgi/content/full/13/supple_4/2.

Ferrario et al. "Survivin, a Member of the Inhibitor of Apoptosis Family, Is Induced by Photodynamic Therapy and Is a Target for Improving Treatment Response." *Cancer Research*. May 15, 2007; 67 (10): 4989-95.

Sydor et al. "Development of 17-allylamino-17-demethoxygeldanamycin hydroquinone hydrochloride (IPI-504), an anti-cancer agent directed against Hsp90." *Proc. Natl. Acad. Sci. USA*. Nov. 14, 2006; 103 (46): 17408-13.

(56) References Cited

OTHER PUBLICATIONS

Blank et al. "Enhanced Ubiquitinylation of Heat Shock Protein 90 as a Potential Mechanism for Mitotic Cell Death in Cancer Cells Induced with Hypericin." *Cancer Research*. Dec. 1, 2003; 63 (23): 8241-7.

Schneider-Yin et al. "Hypericin and 5-aminolevulinic acid-induced protoporphyrin IX induce enhanced phototoxicity in human endometrial cancer cells with non-coherent white light." *Photodiagnosis Photodynamic Therapy*. Mar. 2009; 6 (1): 12-18.

Lilge et al. "Apoptosis induced in vivo by photodynamic therapy in normal brain and intracranial tumour tissue." *British Journal of Cancer*. Oct. 2000; 83 (8): 1110-7.

Ortel et al. "Differentiation enhances aminolevulinic acid-dependent photodynamic treatment of LNCaP prostate cancer cells." *British Journal of Cancer*. Nov. 18, 2002; 87 (11): 1321-7.

Gomer et al. "Photodynamic Therapy: Combined Modality Approaches Targeting the Tumor Microenvironment." *Lasers in Surgery and Medicine*. Jun. 2006; 38 (5): 516-21.

Song et al. "Antitumor activity and molecular effects of the novel heat shock protein 90 inhibitor, IPI-504, in pancreatic cancer." *Molecular Cancer Therapeutics*. Oct. 2008; 7 (10): 3275-84.

Patterson et al. "IPI-S04, a novel and soluble HSP-90 inhibitor, blocks the unfolded protein response in multiple myeloma cells." *Cancer Chemother. Pharmacol*. May 2008; 61 (6): 923-32.

Abramson et al. "The heat shock protein 90 inhibitor IPI-S04 induces apoptosis of AKT—dependent diffuse large 8-cell lymphomas." *Br. J. Haematology*. Feb. 2009; 144 (3): 358-66.

Ferrario et al. "Targeting the 90 kDa Heat Shock Protein Improves Photodynamic Therapy." *Cancer Lett*. Mar. 2010; 289: 188-94.

Nagae, T.; Aizawa, K.; Uchimura, N.' Tani, D.; Abe, M.; Fujishima, K.; Wilson, S.; and Ishimaru, S. "Endovascular Photodynamic Therapy Using Mono-L-Aspartyl-Chlorin e6 to Inhibit Intimal Hyperplasia in Balloon-Injured Rabbit Arteries," *Lasers in Surgery and Medicine*, 28:381-388 (2001). © 2001 Wiley-Liss, Inc.

Nordenström, Björn. "Balloon Catheters for Percutaneous Insertion Into the Vascular System," Department of Diagnostic Roentgenology, Thoraxkliniken, Karolinska Sjukhuset, Stockholm, Sweden. pp. 411-416.

Nordenström, Björn. "New Instruments for Catheterization and Angiocardiography," Department of Roentgenology, Thoraxkliniken,Karolinska Sjukhuset, Stockholm, Sweden. Aug. 1965. pp. 256-259.

Weber, Jeffrey., "Review: Anti-CTLA-4 Antibody Ipilmumab: Case Studies of Clinical Response and Immune-Related Adverse Events." *The Oncologist*, vol. 12: 864-872, 2007.

N.a., "Photodynamic Therapy for Cancer Fact Sheet." *National Cancer Institute*: pp. 1-3, 2004.

\* cited by examiner

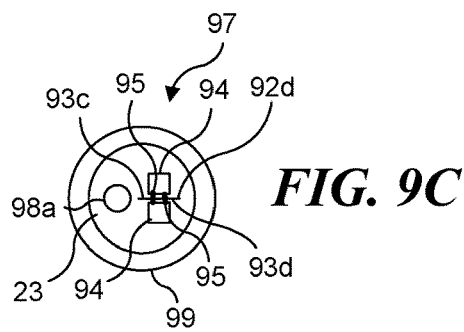
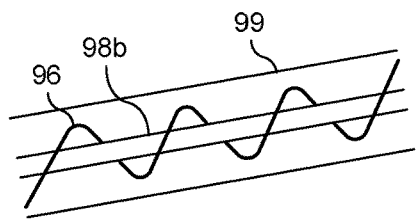
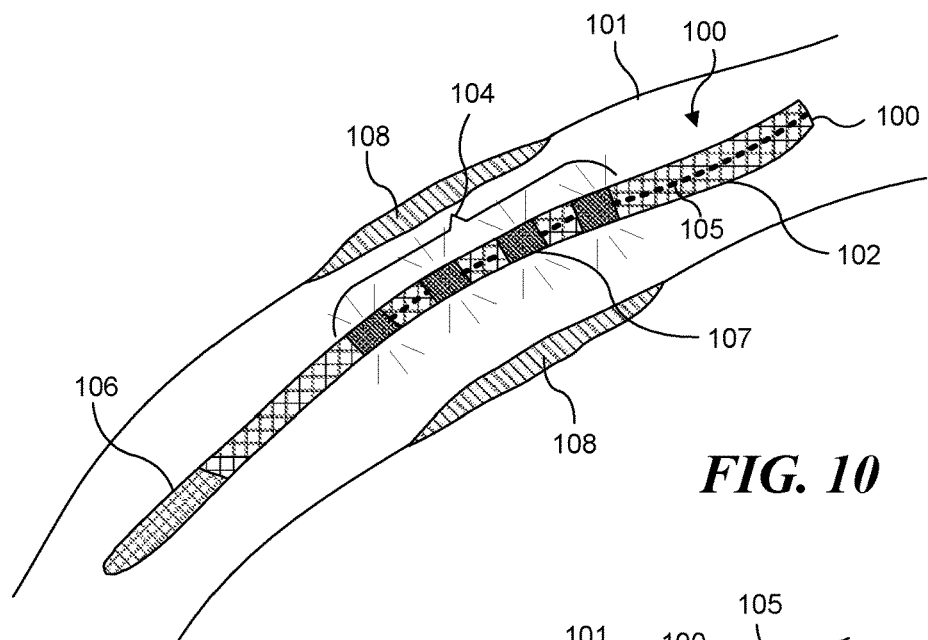
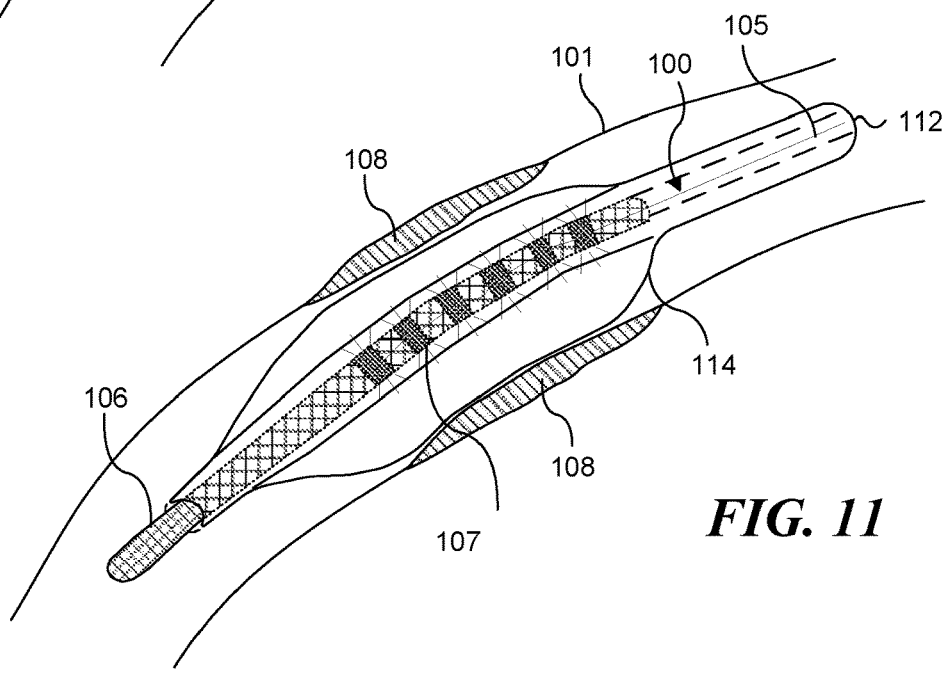

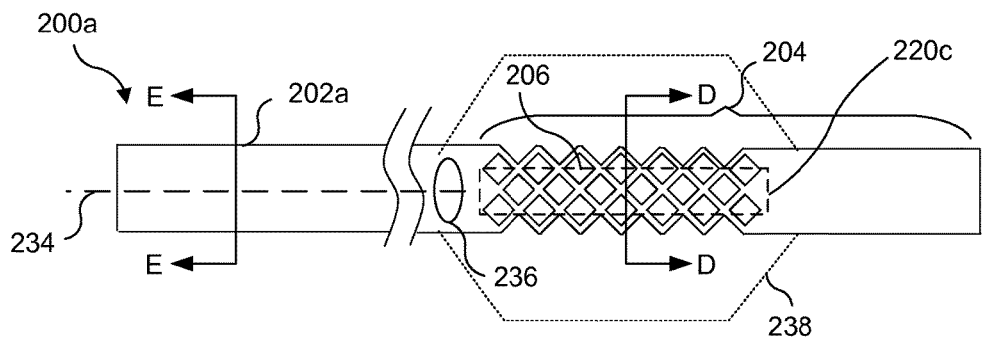
FIG. 13N
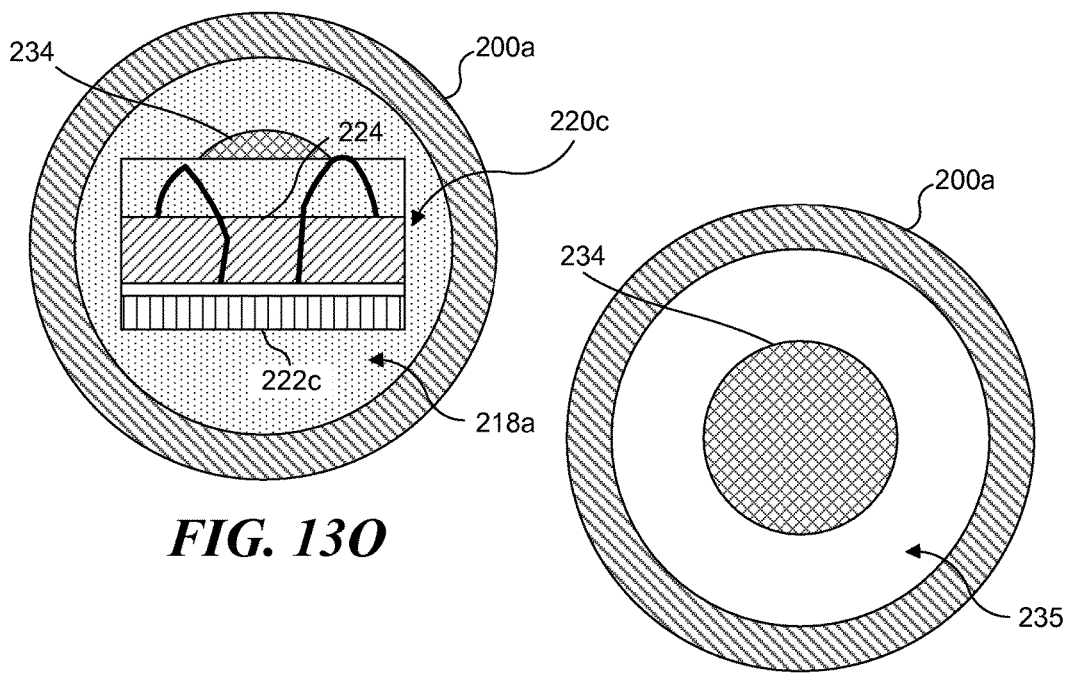
FIG. 13O
FIG. 13P

LIGHT GENERATING GUIDE WIRE FOR INTRAVASCULAR USE

RELATED APPLICATIONS

This application is a continuation-in-part application of a copending patent application Ser. No. 10/799,357, filed on Mar. 12, 2004, which itself is based on a prior provisional application Ser. No. 60/455,069, filed on Mar. 14, 2003, the benefit of the filing dates of which are hereby claimed under 35 U.S.C. § 119(e) and 120.

BACKGROUND

Photodynamic therapy (PDT) is a process whereby light of a specific wavelength or waveband is directed to tissues undergoing treatment or investigation, which have been rendered photosensitive through the administration of a photoreactive or photosensitizing agent. Thus, in this therapy, a photoreactive agent having a characteristic light absorption waveband is first administered to a patient, typically by intravenous injection, oral administration, or by local delivery to the treatment site. Abnormal tissue in the body is known to selectively absorb certain photoreactive agents to a much greater extent than normal tissue. Once the abnormal tissue has absorbed or linked with the photoreactive agent, the abnormal tissue can then be treated by administering light of an appropriate wavelength or waveband corresponding to the absorption wavelength or waveband of the photoreactive agent. Such treatment can result in the necrosis of the abnormal tissue.

PDT has proven to be very effective in destroying abnormal tissue such as cancer cells and has also been proposed for the treatment of vascular diseases, such as atherosclerosis and restenosis due to intimal hyperplasia. In the past percutaneous transluminal coronary angioplasty (PTCA) has typically been performed to treat atherosclerotic cardiovascular diseases. A more recent treatment based on the use of drug eluting stents has reduced the rate of restenosis in some diseased vessels. As effective as such therapies are, a new platform of therapy is needed for treating peripheral arterial disease and more problematic coronary diseases, such as vulnerable plaque, saphenous vein bypass graft disease, and diffuse long lesions.

The objective of PDT may be either diagnostic or therapeutic. In diagnostic applications, the wavelength of light is selected to cause the photoreactive agent to fluoresce, thus yielding information about the tissue without damaging the tissue. In therapeutic applications, the wavelength of light delivered to the tissue treated with the photoreactive agent causes the photoreactive agent to undergo a photochemical reaction with oxygen in the localized tissue, to yield free radical species (such as singlet oxygen), which cause localized cell lysis or necrosis. The central strategy to inhibit arterial restenosis using PDT, for example, is to cause a depletion of vascular smooth muscle cells, which are a source of neointima cell proliferation (see, Nagae et al., *Lasers in Surgery and Medicine* 28:381-388, 2001). One of the advantages of PDT is that it is a targeted technique, in that selective or preferential delivery of the photoreactive agent to specific tissue enables only the selected tissue to be treated. Preferential localization of a photoreactive agent in areas of arterial injury, with little or no photoreactive agent delivered to healthy portions of the arterial wall, can therefore enable highly specific PDT ablation of arterial tissue.

Light delivery systems for PDT are well known in the art. Delivery of light from a light source, such as a laser, to the treatment site has been accomplished through the use of a single optical fiber delivery system with special light-diffusing tips affixed thereto. Exemplary prior art devices also include single optical fiber cylindrical diffusers, spherical diffusers, micro-lensing systems, an over-the-wire cylindrical diffusing multi-optical fiber catheter, and a light-diffusing optical fiber guidewire. Such prior art PDT illumination systems generally employ remotely disposed high power lasers or solid state laser diode arrays, coupled to optical fibers for delivery of light to a treatment site. The disadvantages of using laser light sources include relatively high capital costs, relatively large size, complex operating procedures, and the safety issues inherent when working with high power lasers. Accordingly, there is a tremendous need for a light generating system that requires no lasers, and which generates light at the treatment site. For vascular application of PDT, it would be desirable to provide a light-generating apparatus having a minimal cross-section, a high degree of flexibility, and compatibility with a guidewire, so the light-generating apparatus can be delivered to the treatment site. Such an apparatus should provide a light uniformly to the treatment area.

For vascular application of PDT, it would be further desirable to provide a light-generating apparatus configured to be centered within a blood vessel, and which is configured to remove light absorbent material, such as blood, from the light path between the target tissue and the apparatus. Typically, centering of apparatus within a vessel can be achieved with an inflatable balloon catheter that matches the diameter of the blood vessel when the balloon is inflated. Such devices desirably occlude blood flow, enabling the light path to remain clear of obstructing blood. However, a single balloon is not sufficient to treat lesions in coronary blood vessels that are greater than about 30 mm in length, because a single inflated balloon may not provide good centering of the apparatus within such a long section. Therefore, it would be desirable to provide a light-generating apparatus that is configured to treat long lesions or long vessel segments.

SUMMARY

The concepts disclosed herein encompass exemplary light generating devices for illuminating portions of vascular tissue to enable PDT to be provided. Each embodiment includes one or more light sources configured to be positioned inside a body cavity or a vascular system. While the term "light source array" is frequently employed herein, because certain exemplary embodiments of the concepts disclosed herein include multiple light sources arranged in a radial or linear configuration, it should be understood that a single light source could also be employed. Using a plurality of light sources enables larger treatment areas to be illuminated. Light emitting diodes (LEDs) are particularly useful as light sources, although other types of light sources can alternatively be employed, as described in detail below. The light source that is used is selected based on the characteristics of a photoreactive agent with which the apparatus is intended to be used for rendering PDT, since light of inappropriate wavelengths will not cause the desired reaction by the photoreactive agent. Light source arrays can include light sources that provide more than one wavelength or waveband of light. The shape of the light source array can be selected to match the shape of a desired area to be treated with PDT. For example, linear light source arrays are particularly useful to treat elongate regions of tissue. Light source arrays can also include reflective elements to enhance the transmission of light in a desired direction.

An important aspect of the concepts disclosed herein is directed to the incorporation of light emitting devices, such as LEDs, in a guidewire. Such a guidewire is used with a catheter, such as one including one or more expandable members. In a first exemplary embodiment, a conventional guidewire is modified to include a conductive core enabling light sources to be coupled to an external power supply, and a plurality of orifices are formed into the distal end of the guidewire. The orifices extend to the conductive core, so that light sources can be inserted into the orifices and electrically coupled to the conductive core. Each light source is then electrically coupled through the conductive core to an external lead that enables a complete circuit to be achieved to energize the light sources. The distal end of the guidewire and light sources are then covered with a flexible polymer, which should be substantially optically transparent in regard to the wavelength or waveband of light being emitted by the light sources, at least where the flexible polymer overlies the light sources.

In a second exemplary embodiment, a hollow tube (such as a nitinol hypotube) is used as a guidewire, and a light source array (such as a linear LED array) is disposed at a distal end of the hollow tube. A plurality of openings are formed in the distal end of the hollow tube, and the array is disposed such that the array is surrounded by the plurality of openings. In one exemplary embodiment, a pair of wires extends from the array through the hollow tube to a proximal end of the hollow tube, to enable the array to be selectively energized. In an alternative exemplary embodiment, the hollow tube is coated with a conductive material such that the conductive coating on the hollow tube functions as one of the wires, and then only a single wire is required to extend from the array through hollow tube, to its proximal end. A potting compound encapsulates the array. The potting compound is electrically insulating and optically transparent to the light emitted by the array.

Guidewires including integral light sources are employed in the following manner. The guidewire is introduced into a body lumen (preferably a blood vessel) until the light sources are disposed proximate to a treatment site. A catheter including an inflatable member is advanced over the guidewire to the treatment site, such that the inflatable member is disposed proximate to the treatment site. The expandable member is expanded, thereby centering the guidewire in the body lumen. The light sources are then energized to provide the PDT treatment.

The expandable member is disposed so as to substantially encompass the light source array in one exemplary embodiment. Accordingly, the catheter includes an inflation lumen to enable the expandable member to be inflated. Each end of the light source array in the guidewire of this embodiment is marked with a radio-opaque tag (or some other type of identifier) so that the light source array can be properly positioned adjacent to target tissue. The length of the linear array is only limited by the length of the expandable member. If the linear array is made longer than the expandable member, light emitted from that portion of the linear array extending beyond the expandable member will be blocked by blood, and is not likely to reach the target tissue. As described below, the use of a plurality of expandable members enables longer linear light sources to be used.

Use of a linear light source array in a guidewire configured in accord with the concepts disclosed herein requires that the array be sufficiently flexible to enable the resulting guidewire to be advanced through a vascular system. LEDs are sufficiently small and compact, so that when LEDs are mounted to a flexible conductive substrate, a flexible linear light source array is achieved that meets this requirement. The flexibility of the linear light source array can be further enhanced by including strain relief elements in the light source array. If necessary, strain relief features can be incorporated into the guidewire itself to enhance flexibility. Also, including a plurality of folds or bends in the flexible conductive substrate will further enhance the flexibility of the substrate. The polymer employed to encapsulate the LEDs and conductive substrate is selected to be both optically transparent to the wavelength of the light used, and sufficiently flexible to enable the linear array to be advanced through a vascular system that includes substantial bends.

The exemplary embodiments described above are used with a photoreactive agent that is introduced into the target area prior to the apparatus being introduced into the blood vessel. However, it will be understood that if desired, the catheter used in connection with the guidewires disclosed herein can optionally include a lumen for delivering a photoreactive agent into the target area. The hollow guidewire itself can also include such a drug delivery lumen. The resulting exemplary embodiments are likely to be particularly beneficial where uptake of the photoreactive agent into the target tissues is relatively rapid, so that the apparatus does not need to remain in the blood vessel for an extended period of time while the photoreactive agent is distributed into and absorbed by the target tissue.

With respect to expandable members, such elements can beneficially include inflatable balloons to enable the guidewire to be centered in a blood vessel, and if desired, to occlude blood flow in the region of treatment (since blood can interfere with the transmission of light from the light source to the intended target tissue).

In configurations where light is intended to be directed through such expandable members to reach target tissue, the expandable members can be constructed from materials that substantially transmit the wavelength of light being emitted by the light sources. Bio-compatible polymers having the required optical characteristics are particularly useful for this purpose. Where light is directed through such expandable members to reach target tissue, a fluid used to inflate the expandable members can include additives to enhance the transmission or diffusion of light. In configurations where an expandable member is disposed proximate to a light source array, the fluid used to expand the member acts as a heat sink to absorb heat generated by the light source array. Regularly replacing the fluid within the expandable member will enhance the cooling effects. Positioning aids, such as radio-opaque markers, can be included in the devices to enable any of the embodiments described in detail below to be properly positioned with respect to a target area.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 schematically illustrates a first embodiment of a light-generating apparatus suitable for intravascular use in accord with the present invention;

Figure 2:
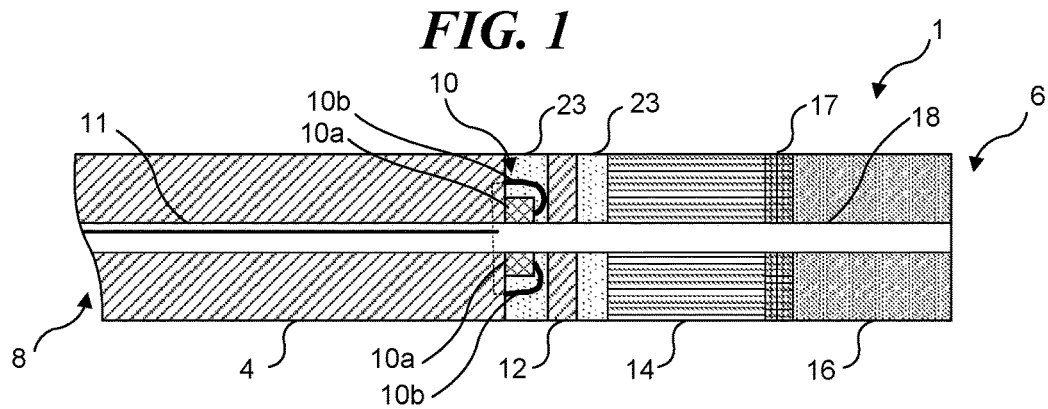
FIG. 2 is a longitudinal cross-sectional view of the light-generating apparatus of FIG. 1.
Figure 4A:
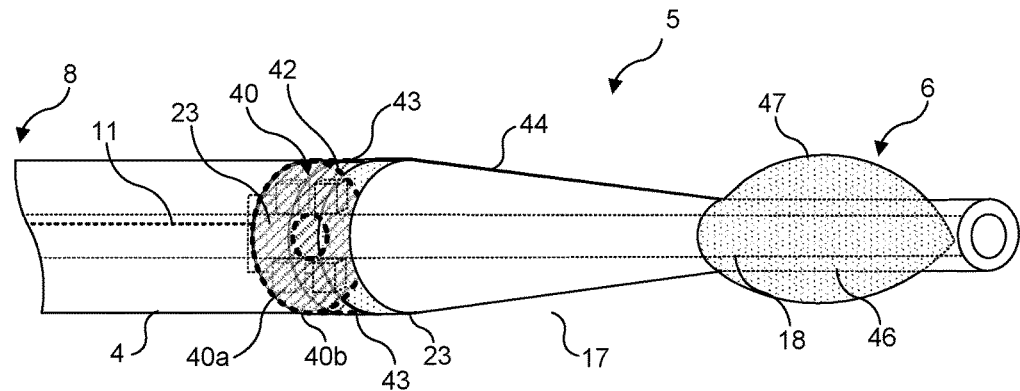
Figure 4B:
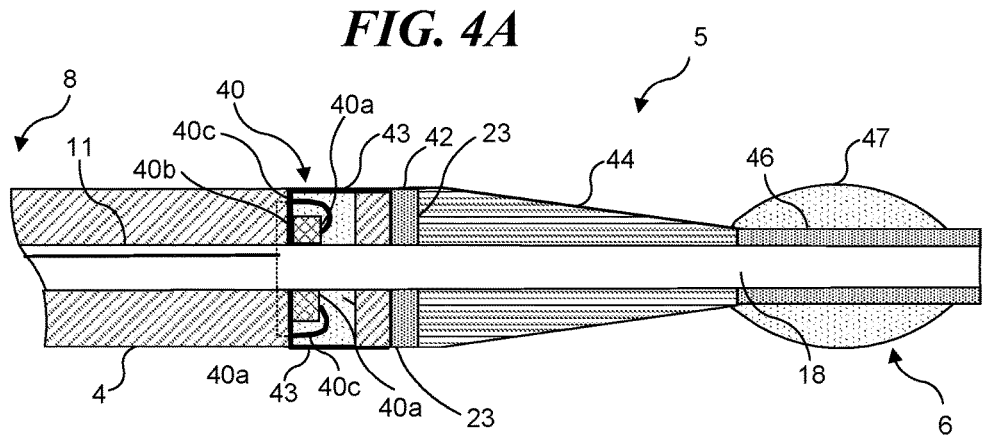
Figure 5:
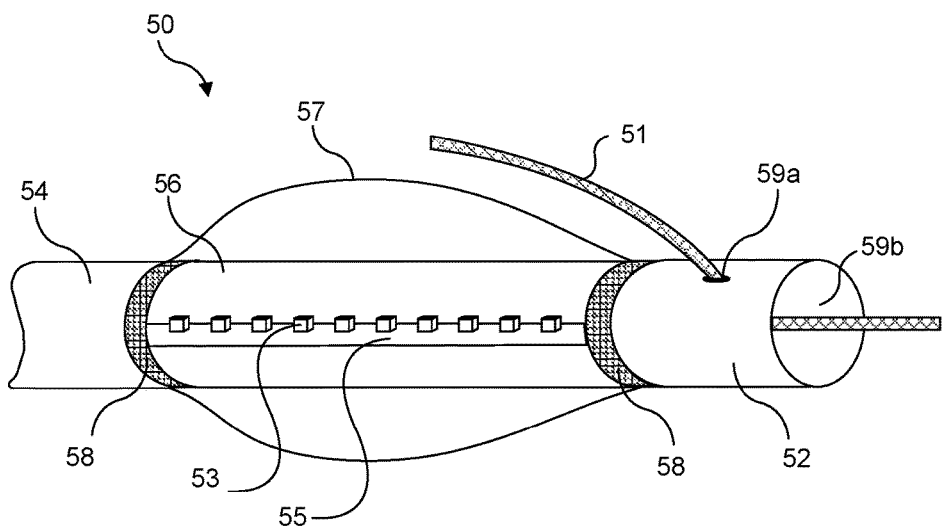
Figure 6:
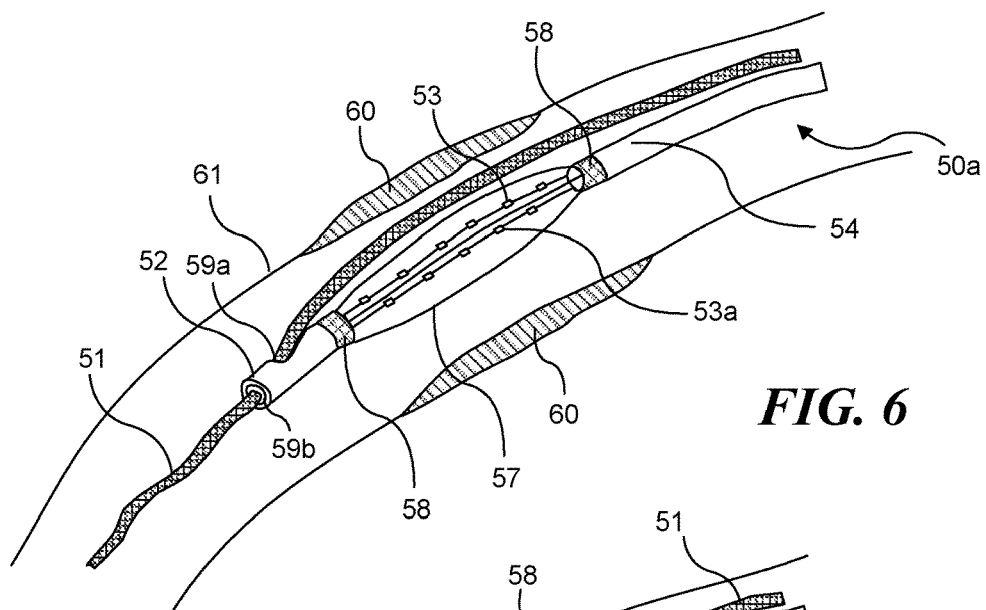
Figure 7:
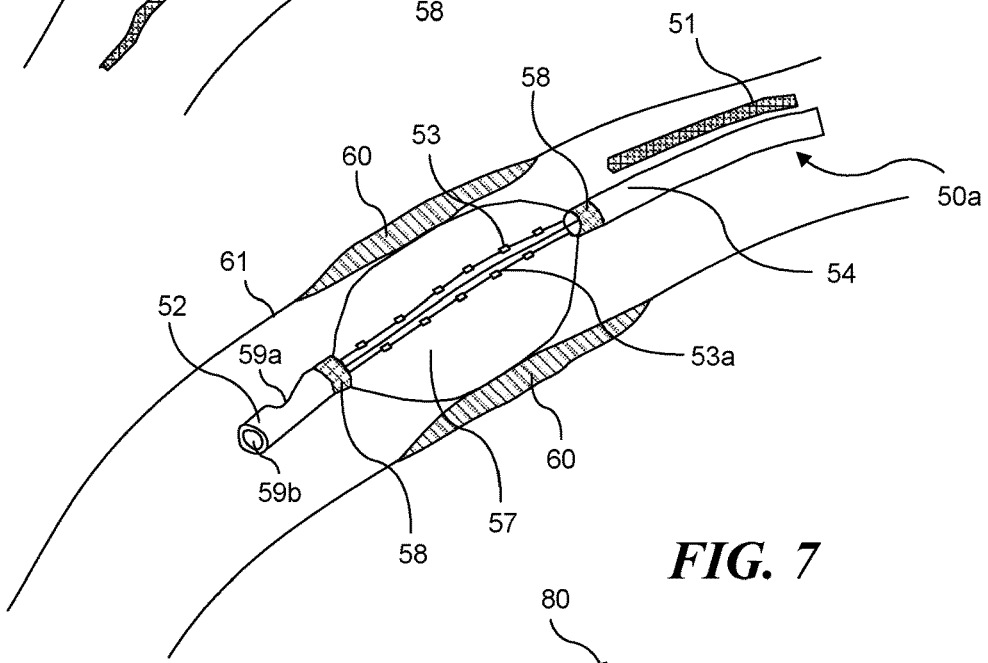
Figure 8:
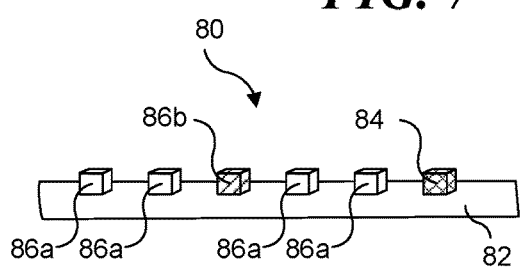
Figure 9A:
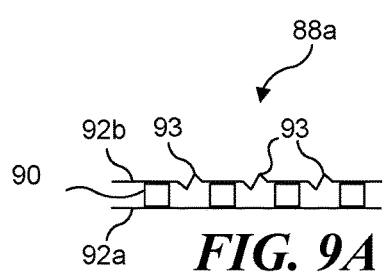
Figure 9B:
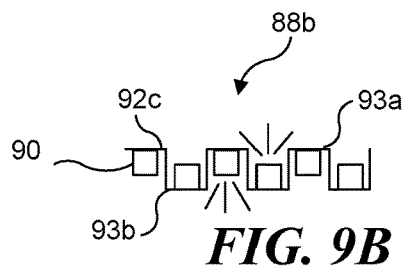
Figure 12A:
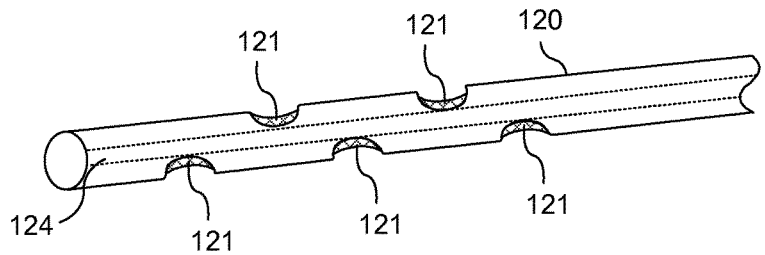
Figure 12B:
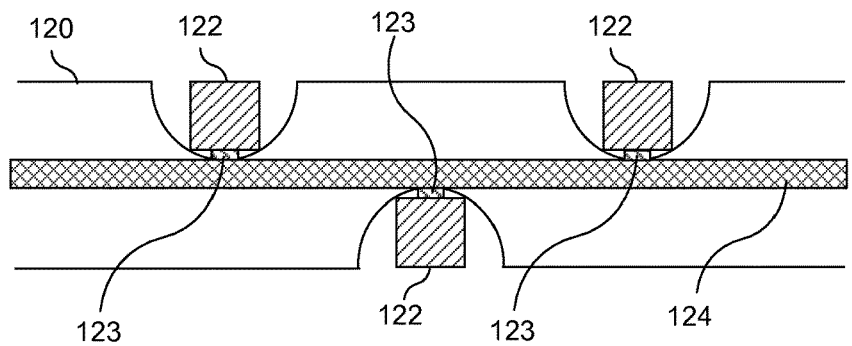
Figure 12C:
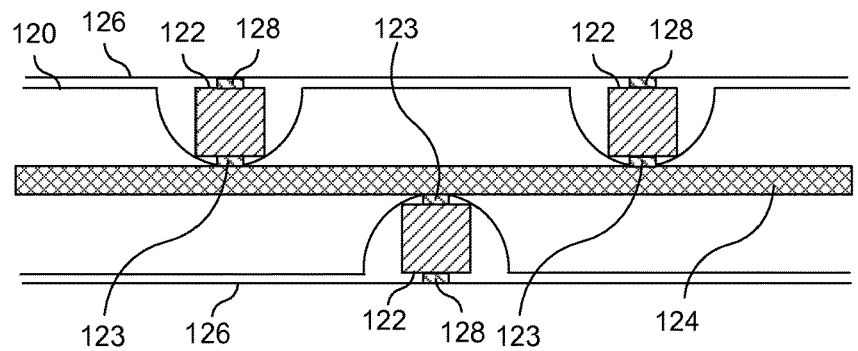
Figure 12D:
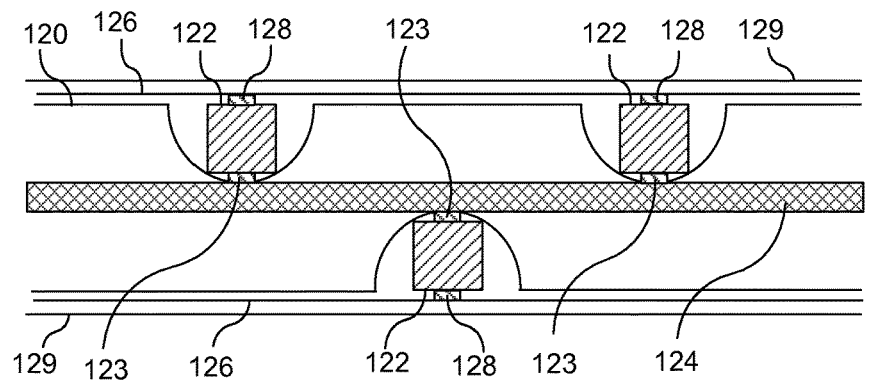
Figure 13A:
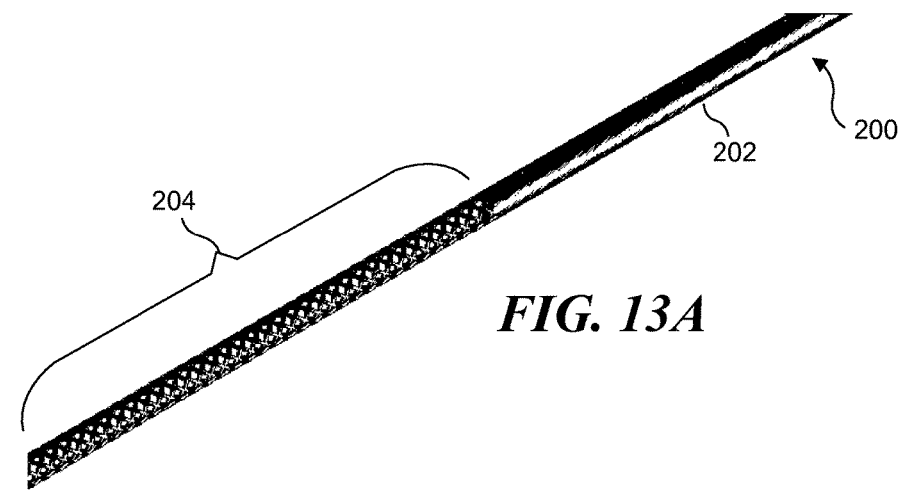
Figure 13B:
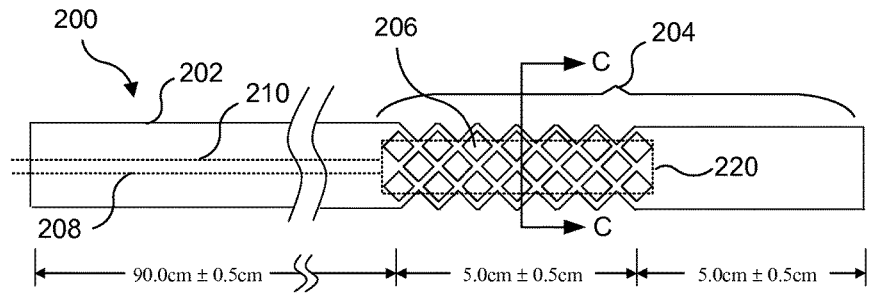
Figure 13C:
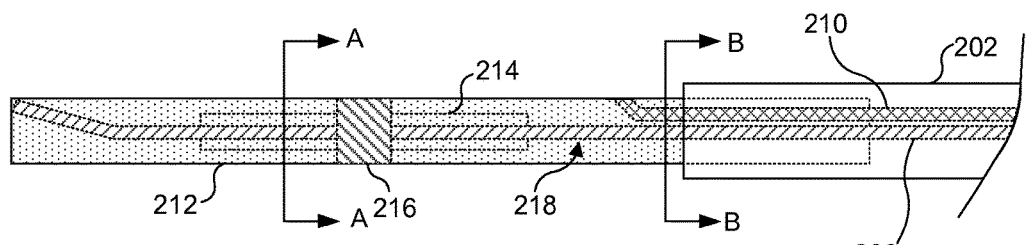
Figure 13D:
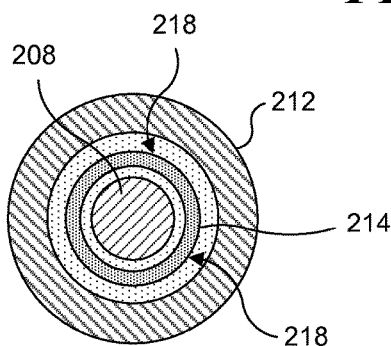
Figure 13E:
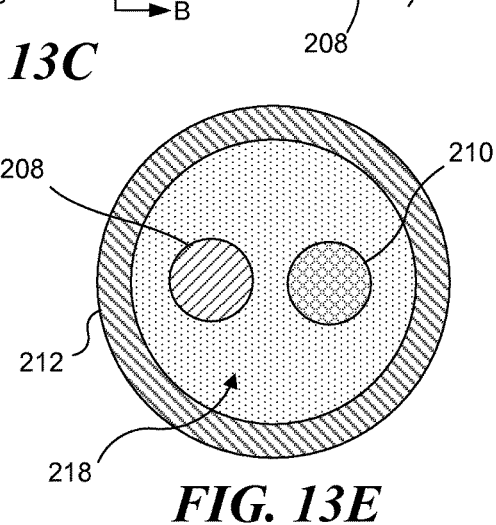
Figure 13F:
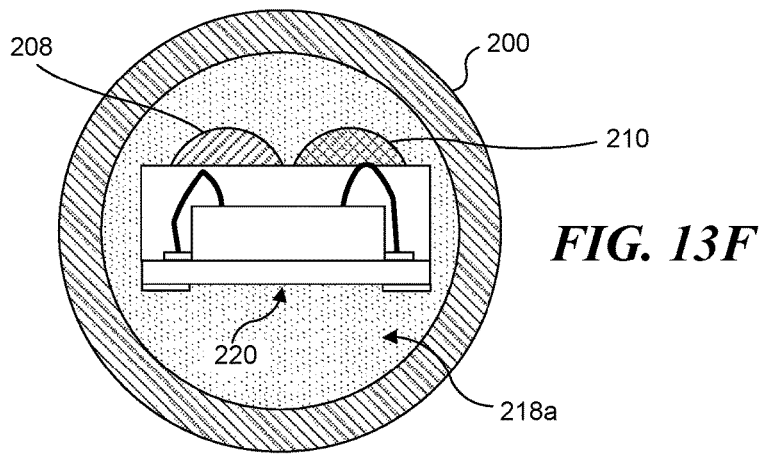
Figure 13G:
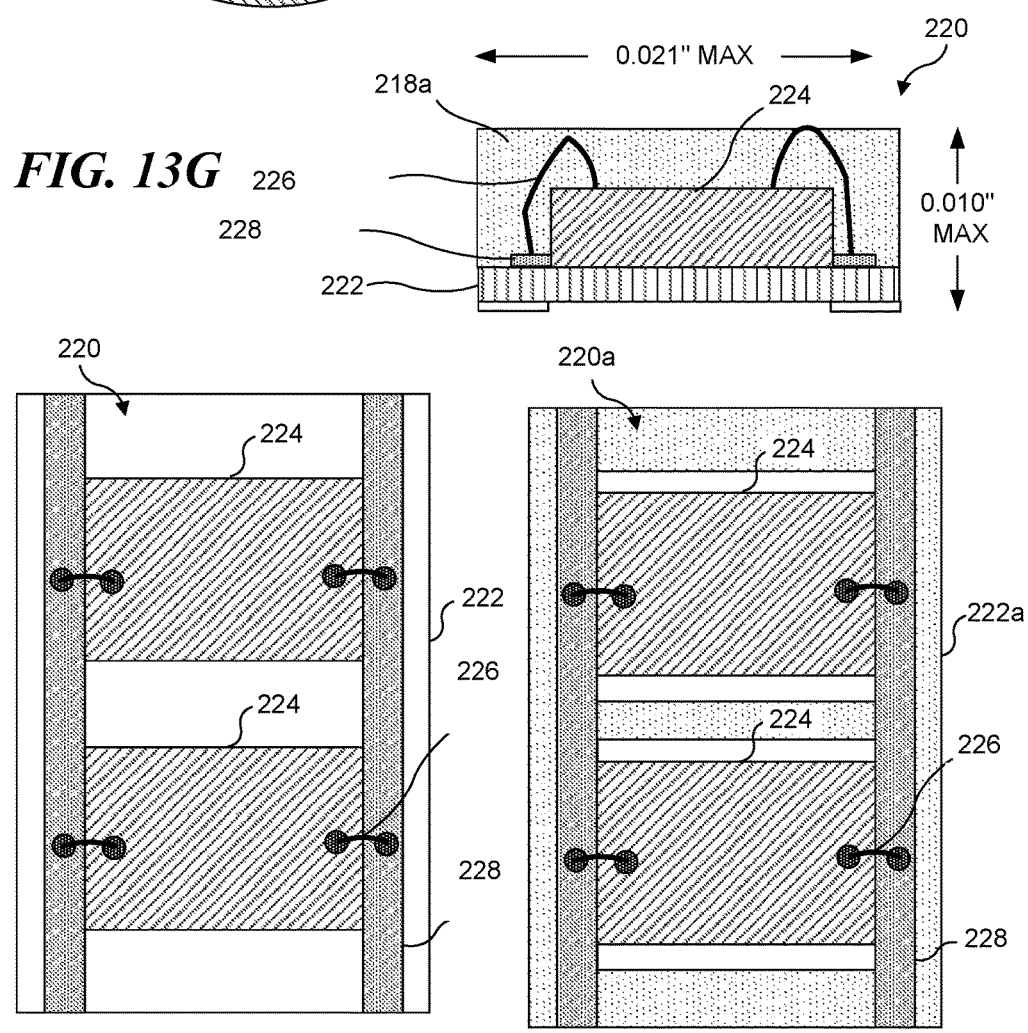
Figure 13J:
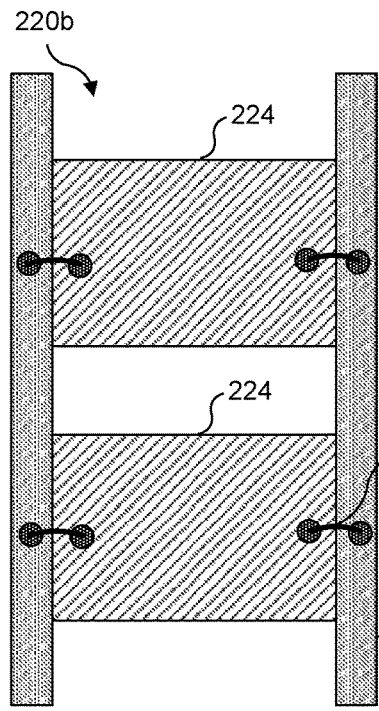
Figure 13K:
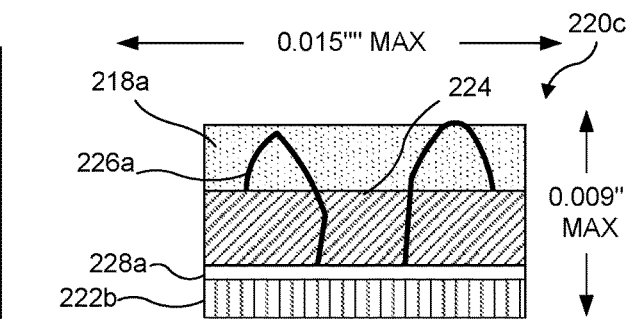
Figure 13L:
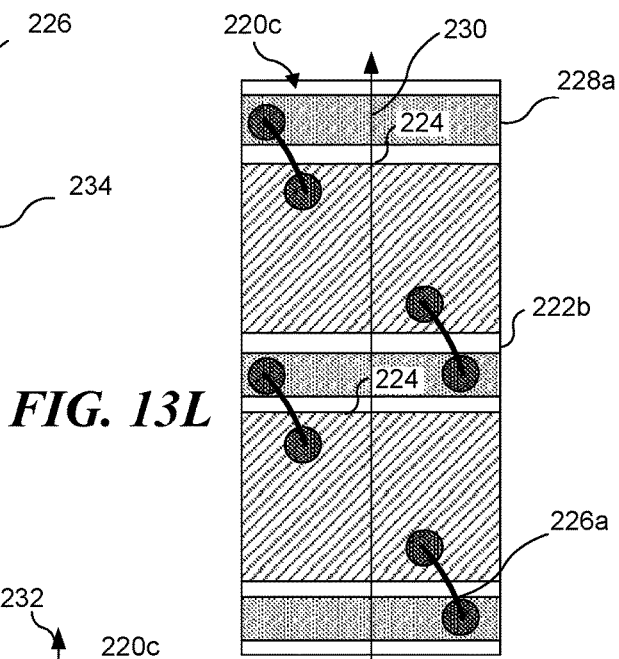
Figure 13M:
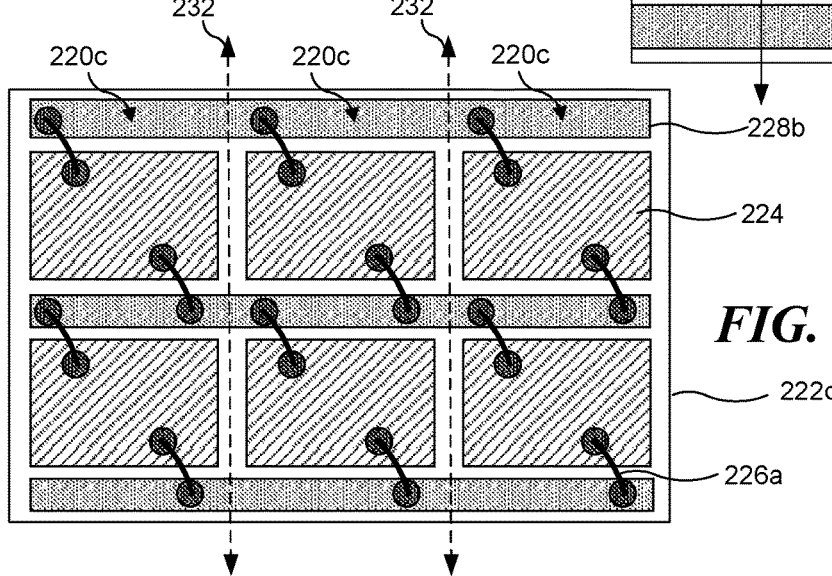
Figure 14A:
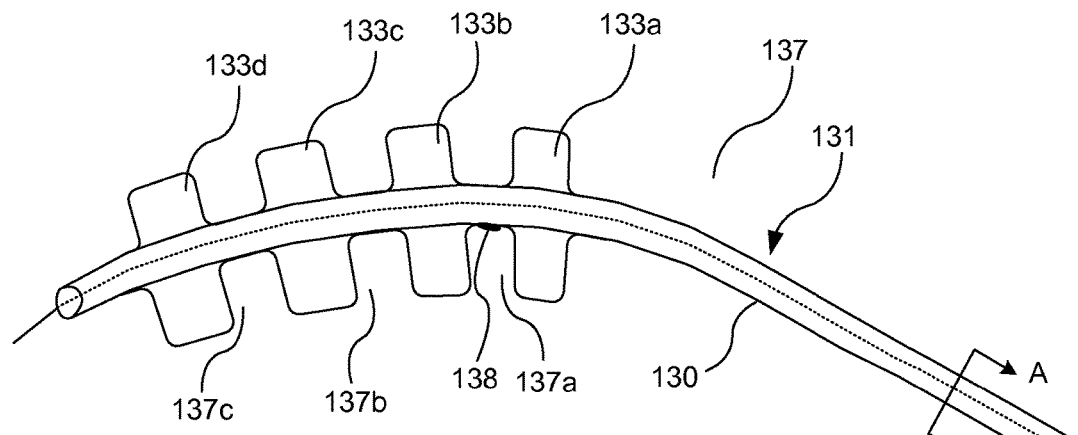
Figure 14B:
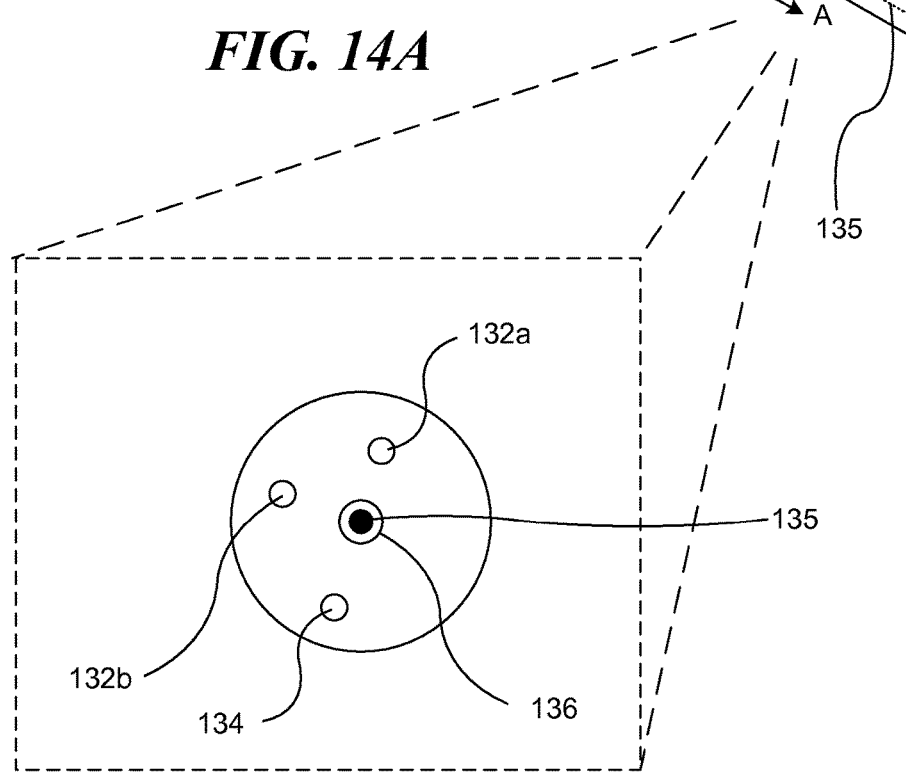
Figure 14C:
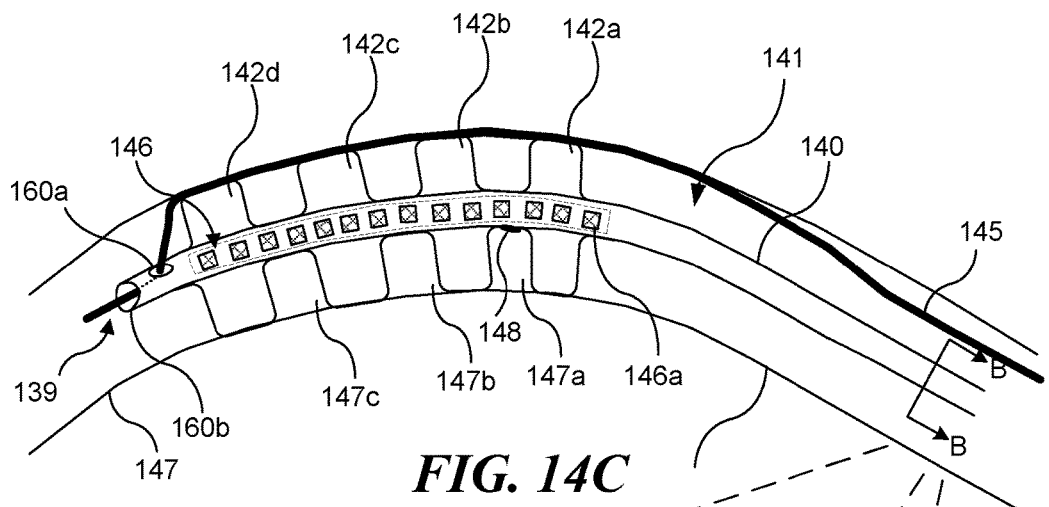
Figure 14D:
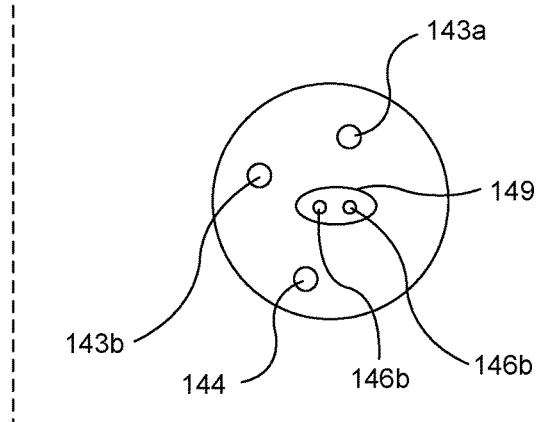
Figure 15:
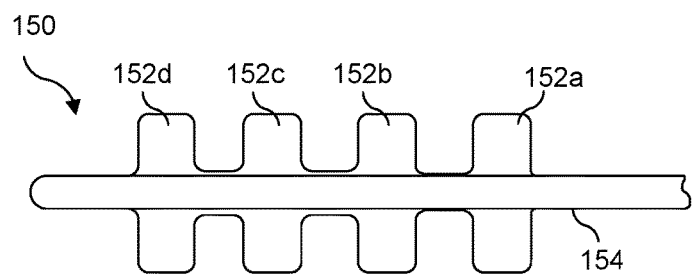
Figure 16A:
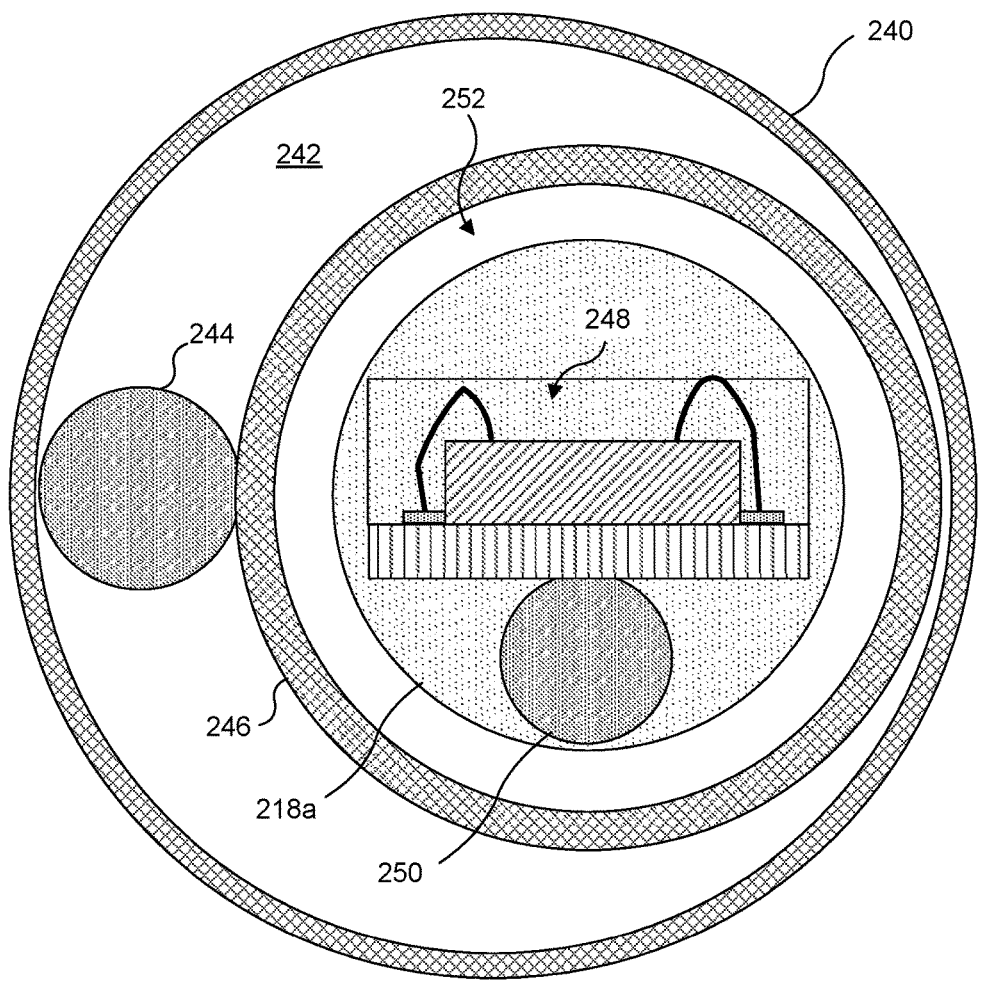
Figure 16B:
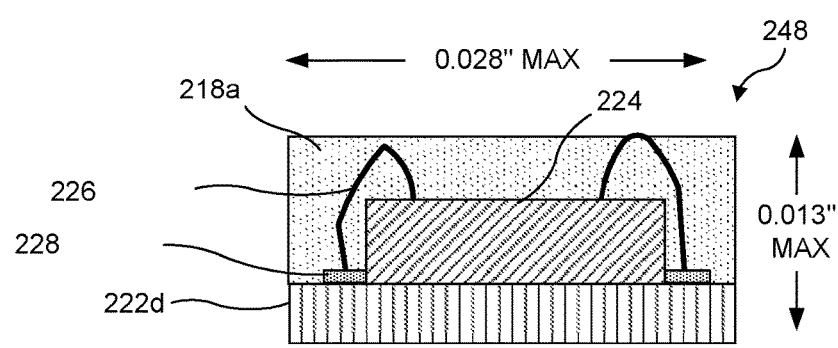

FIG. 4A schematically illustrates a second embodiment of a light-generating apparatus suitable for intravascular use in accord with the present invention;

FIG. 4B is a longitudinal cross-section view of the light-generating apparatus of FIG. 2;

FIG. 5 schematically illustrates yet another embodiment of a light-generating apparatus suitable for intravascular use in accord with the present invention;

FIG. 6 schematically illustrates the light-generating apparatus of FIG. 5 being positioned within a blood vessel;

FIG. 7 schematically illustrates the light-generating apparatus of FIGS. 5 and 6 being activated within a blood vessel;

FIG. 8 schematically illustrates a multicolor light array for use in the light-generating apparatus of FIG. 5;

FIGS. 9A and 9B schematically illustrate configurations of light arrays including strain relief features for enhanced flexibility for use in a light-generating apparatus in accord with the present invention;

FIG. 9C is cross-sectional view of a light-generating apparatus in accord with the present invention, showing one preferred configuration of how the light emitting array is positioned relative to the guidewire used to position the light-generating apparatus;

FIG. 9D schematically illustrates a portion of a light-generating apparatus in accord with the present invention, showing how in another preferred configuration, the light emitting array is positioned relative to the guidewire used to position the light-generating apparatus;

FIG. 10 schematically illustrates an embodiment of a light-generating apparatus in which light emitting elements are incorporated into a guidewire, as the apparatus is being positioned within a blood vessel;

FIG. 11 schematically illustrates another embodiment of a light-generating apparatus, in which light emitting elements are incorporated into a guidewire and which includes an inflatable balloon, showing the apparatus being positioned within a blood vessel;

FIG. 12A schematically illustrates a modified guidewire for use in the light-generating apparatus of FIGS. 10 and 11;

FIGS. 12B-12D are cross-sectional views of the guidewire of FIG. 12A, showing details of how the light emitting elements are integrated into the guidewire;

FIGS. 13A and 13B schematically illustrate a hollow guidewire including a light source array disposed at its distal end;

FIG. 13C schematically illustrates a connection jack that can be used to electrically couple the array in the hollow guidewire of FIGS. 13A and 13B to a power source;

FIG. 13D is a cross-sectional view of the connection jack taken along section line A-A of FIG. 13C;

FIG. 13E is a cross-sectional view of the connection jack taken along section line B-B of FIG. 13C;

FIG. 13F is a cross-sectional view of the guidewire of FIGS. 13A and 13B taken along section line C-C of FIG. 13B;

FIG. 13G is a side view of a first exemplary array for the guidewire of FIGS. 13A and 13B;

FIG. 13H is a plan view of the first exemplary array for the guidewire of FIGS. 13A and 13B;

FIG. 13I is a plan view of a second exemplary array for the guidewire of FIGS. 13A and 13B;

FIG. 13J is a plan view of a third exemplary array for the guidewire of FIGS. 13A and 13B;

FIG. 13K is a side view of a fourth exemplary array for the guidewire of FIGS. 13A and 13B;

FIG. 13L is a plan view of the fourth exemplary array for the guidewire of FIGS. 13A and 13B;

FIG. 13M is a plan view of a large array from which the fourth exemplary array can be removed for facilitating manufacturing of the fourth exemplary array;

FIG. 13N schematically illustrates yet another hollow guidewire including a light source array disposed at its distal end;

FIG. 13O is a cross-sectional view of the hollow guidewire of FIG. 13N taken along section line D-D of FIG. 13N;

FIG. 13P is a cross-sectional view of the hollow guidewire of FIG. 13N taken along section line E-E of FIG. 13N;

FIG. 14A schematically illustrates still another embodiment of a light-generating apparatus, which includes a plurality of inflatable balloons, as the apparatus is being positioned within a blood vessel;

FIG. 14B is a cross-sectional view of the light-generating apparatus of FIG. 14A;

FIG. 14C schematically illustrates an alternative configuration of a light-generating apparatus including a plurality of inflatable balloons, as the apparatus is being positioned within a blood vessel;

FIG. 14D is a cross-sectional view of the light-generating apparatus of FIG. 14C;

FIG. 15 schematically illustrates a plurality of balloons included with a light-generating apparatus in accord with the present invention;

FIG. 16A is a cross-sectional view of a light emitting catheter disposed in a central lumen of an introducer catheter; and FIG. 16B is a side view of a light source array for use in the light emitting catheter of FIG. 16A.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Unless otherwise defined, it should be understood that each technical and scientific term used herein and in the claims that follow is intended to be interpreted in a manner consistent with the meaning of that term as it would be understood by one of skill in the art to which this invention belongs. The drawings and disclosure of all patents and publications referred to herein are hereby specifically incorporated herein by reference. In the event that more than one definition is provided herein, the explicitly defined definition controls.

Figure 1:
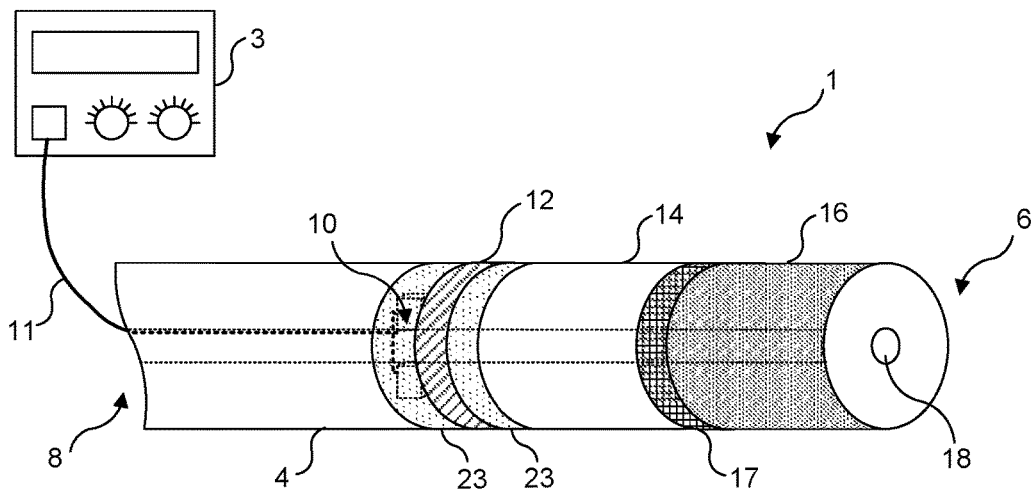

Referring to FIG. 1, a light-generating apparatus 1, having a distal end 6 and a proximal end 8, is embodied in a catheter having an elongate, flexible body 4 formed from a suitable biocompatible material, such as a polymer or metal. Catheter body 4 includes at least one lumen 18. While lumen 18 is shown as centrally disposed within catheter body 4, it should be understood that lumen 18 can be disposed in other positions, and that other lumens, such as lumens for inflating a balloon or delivering a fluid (neither separately shown) can also be included and disposed at locations other than along a central axis of catheter body 4. Lumen 18 has a diameter sufficient to accommodate a guidewire and extends between distal end 6 and proximal end 8 of the catheter, passing through each portion of light-generating apparatus 1. FIG. 1 is not drawn to scale, and a majority of light-generating apparatus 1 shown in FIG. 1 relates to elements disposed near distal end 6. It should be understood that light-generating apparatus 1 is preferably of sufficient length to be positioned so that distal end 6 is disposed at a treatment site within a patient's body, while proximal end 8 is disposed outside of the patient's body, so that a physician or surgeon can manipulate light-generating apparatus 1 with the proximal end.

A light source array 10 includes a plurality of light emitting devices, which are preferably LEDs disposed on conductive traces electrically connected to lead 11. Lead 11 extends proximally through lumen 18 and is coupled to an external power supply and control device 3. While lead 11 is shown as a single line, it should be understood that lead 11 includes at least two separate conductors, enabling a complete circuit to be formed that supplies current to the light emitting devices from the external power supply. As an alternative to LEDs, other sources of light may instead be used, including but not limited to: organic LEDs, super luminescent diodes, laser diodes, and light emitting polymers. In a preferred embodiment, each LED of light source array 10 is encapsulated in a polymer layer 23. Preferably, collection optics 12 are similarly encapsulated in polymer layer 23. Light source array 10 is preferably coupled to collection optics 12, although it should be understood that collection optics 12, while preferred, are not required. When present, collection optics 12 are coupled to either a single optical fiber 14, or an optical fiber bundle (not separately shown). Distal to optical fiber 14 is a light-diffusing tip 16, which can be implemented using glass or plastic. Light emitted from light source array 10 passes through collection optics 12, which focus the light toward optical fiber 14. Light conducted along optical fiber 14 enters diffusing tip 16 at distal end 6 and is scattered uniformly. Preferably, diffusing tip 16 includes a radio-opaque marker 17 to facilitate fluoroscopic placement of distal end 6.

FIG. 2 illustrates a longitudinal cross-section view of light-generating apparatus 1. Collection optics 12 (e.g., a lens) are bonded to light source array 10 and optical fiber 14 by polymer layers 23, and the polymer layer is preferably an epoxy that is optically transparent to the wavelengths of light required to activate the photoreactive agent that is being used. Individual LEDs 10a and leads 10b (each coupling to lead 11) can be clearly seen.

Figure 3A:
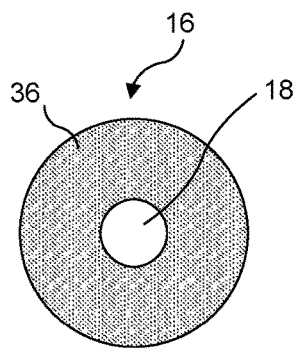
FIGS. 3A and 3B are exemplary radial cross-sectional views of two different embodiments of the light-diffusing portion of the light-generating apparatus of FIG. 1.
Figure 3B:
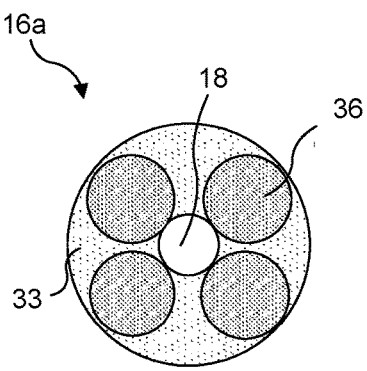

FIG. 3A is a radial cross-sectional view of diffusing tip 16, which includes one diffusing portion 36 and lumen 18. FIG. 3B is a radial cross-sectional view of an alternative diffusing tip 16a, which includes a plurality of diffusing portions 36 encapsulated in a polymer 33, and lumen 18. Polymer 33 preferably comprises an epoxy, and such an epoxy will likely be optically transparent to the wavelengths of light required to activate the photoreactive agent being utilized; however, because the light will be transmitted by diffusion portions 36, polymer 33 is not required to be optically transparent to these wavelengths. In some applications, it may be desirable to prevent light of any wavelength that can activate the photoreactive agent from exiting a light-generating apparatus other than from its distal end, and polymers do not transmit such wavelengths can be used to block such light.

Turning now to FIG. 4A, another embodiment of a light generating catheter is schematically illustrated. A light-generating apparatus 5 is similarly based a catheter having body 4, including lumen 18, and includes distal end 6 and proximal end 8. As discussed above, while only a single lumen configured to accommodate a guidewire is shown, it should be understood that light-generating apparatus 5 can be configured to include additional lumens as well (such as those used for balloon inflation/deflation). Note that FIGS. 4A and 4B are not drawn to scale; with distal end 6 being emphasized over proximal end 8.

Light-generating apparatus 5 includes a light source array 40 comprising a plurality of LEDs 40a (seen in phantom view) that are electrically coupled to lead 11 via leads 40c. As discussed above, light source array 40 is preferably encapsulated in a light-transmissive polymer 23, or at least, in an epoxy that transmits the wavelengths of light required to activate the photoreactive agent introduced into the target tissue. Positioned immediately behind LEDs 40a (i.e., proximal of LEDs 40a) is a highly-reflective disk 40b. Any light emitted from LEDs 40a in a direction toward proximal end 8 is reflected back by reflective disk 40b towards distal end 6. Additionally, a reflective coating 43 (such as aluminum or another reflective material), is applied to the outer surface of body 4 adjacent to light source array 40. Any light from LEDs 40a directed to the sides (i.e., towards body 4) is redirected by reflective coating 43 towards distal end 6. Reflective disk 40b and reflective coating 43 thus cooperatively maximize the intensity of light delivered through distal end 6.

Light source array 40 is coupled to a focusing lens 42, which in turn, is coupled to an optical fiber bundle 44. Preferably, optical fiber bundle 44 tapers toward distal end 6, as shown in FIGS. 4A and 4B; however, it should be understood that this tapered shape is not required. Optical fiber bundle 44 is coupled to a light-diffusing tip 46. An expandable member 47 (such as an inflatable balloon) is included for centering light-generating apparatus 5 within a blood vessel and for occluding blood flow past distal end 6 that could reduce the amount of light delivered to the targeted tissue. The expandable member is preferably secured to distal end 6 so as to encompass light-diffusing tip 46. Expandable member 47 may be formed from a suitable biocompatible material, such as, polyurethane, polyethylene, fluorinated ethylene propylene (PEP), polytetrafluoroethylene (PIPE), or polyethylene terephthalate (PET).

It should be understood that while light source array 40 has been described as including a plurality of LEDs 40a disposed on conductive traces electrically connected to lead 11, light source array 40 can alternatively use other sources of light. As noted above, possible light sources include, but are not limited to, organic LEDs, super luminescent diodes, laser diodes, and light emitting polymers. While not shown in FIGS. 4A and 4B, it should be understood that light-generating apparatus 5 can beneficially incorporate a radio-opaque marker, as described above in conjunction with light-generating apparatus 1 (in regard to radio-opaque marker 17 in FIGS. 1A and 1B).

FIG. 5 schematically illustrates yet another embodiment of a light-generating catheter in accord with the present invention. This embodiment employs a linear light source array configured so that a more elongate treatment area can be illuminated. While the first and second embodiments described above use an elongate light diffusing element to illuminate an elongate treatment area, because the light diffusing elements are directing light, not generating light, increasing the length of the diffusing elements merely distributes the light over a greater area. If diffused over too great an area, insufficient illumination will be provided to each portion of the treatment site. The embodiment shown in FIG. 5 includes a linear light source array that enables an elongate treatment area to be illuminated with a greater amount of light than can be achieved using the embodiments shown in FIGS. 1-4B.

Referring to FIG. 5, light-generating apparatus 50 is illustrated. As with the embodiments described above (i.e., the light-generating apparatus shown in FIGS. 1 and 4), light-generating apparatus 50 is preferably based on a multi-lumen catheter and includes an elongate, flexible body formed from a suitable biocompatible polymer or metal, which includes a distal portion 52 and a proximal portion 54. A plurality of light emitting devices 53 are disposed on a flexible, conductive substrate 55 encapsulated in a flexible cover 56 (formed of silicone or other flexible and light transmissive material). Light emitting devices 53 and conductive substrate 56 together comprise a light source array. Preferably, light emitting devices 53 are LEDs, although other light emitting devices, such as organic LEDs, super luminescent diodes, laser diodes, or light emitting polymers can be employed. Each a light source array preferably ranges from about 1 cm to about 20 cm in length, with a diameter that ranges from about 0.5 mm to about 5 mm. Flexible cover 56 can be optically transparent or can include embedded light scattering elements (such as titanium dioxide particles) to improve the uniformity of the light emitted from light-generating apparatus 50. While not specifically shown, it should be understood that proximal portion 54 includes an electrical lead enabling conductive substrate 56 to be coupled to an external power supply and control unit, as described above for the embodiments that have already been discussed.

The array formed of light emitting devices 53 and conductive substrate 56 is disposed between proximal portion 54 and distal portion 52, with each end of the array being identifiable by radio-opaque markers 58 (one radio-opaque marker 58 being included on distal portion 52, and one radio-opaque marker 58 being included on proximal portion 54). Radio-opaque markers 58 comprise metallic rings of gold or platinum. Light-generating apparatus 50 includes an expandable member 57 (such as a balloon) preferably configured to encompass the portion of light-generating apparatus 50 disposed between radio-opaque markers 58 (i.e., substantially the entire array of light emitting devices 53 and conductive substrate 56). As discussed above, expandable member 57 enables occlusion of blood flow past distal portion 52 and centers the light-generating apparatus. Where expandable member is implemented as a fluid filled balloon, the fluid acts as a heat sink to reduce a temperature build-up caused by light emitting devices 53. This cooling effect can be enhanced if light-generating apparatus 50 is configured to circulate the fluid through the balloon, so that heated fluid is continually (or periodically) replaced with cooler fluid. Preferably, expandable member 57 ranges in size (when expanded) from about 2 mm to 15 mm in diameter. Preferably such expandable members are less than 2 mm in diameter when collapsed, to enable the apparatus to be used in a coronary vessel. Those of ordinary skill will recognize that catheters including an inflation lumen in fluid communication with an inflatable balloon, to enable the balloon to the inflated after the catheter has been inserted into a body cavity or blood vessel are well known. While not separately shown, it will therefore be understood that light-generating apparatus 50 (particularly proximal portion 54) includes an inflation lumen. When light emitting devices 53 are energized to provide illumination, expandable member 57 can be inflated using a radio-opaque fluid, such as Renocal 76™ or normal saline, which assists in visualizing the light-generating portion of light-generating apparatus 50 during computerized tomography (CT) or angiography. The fluid employed for inflating expandable member 57 can be beneficially mixed with light scattering material, such as Intralipid, a commercially available fat emulsion, to further improve dispersion and light uniformity.

Light-generating apparatus 50 is distinguished from light-generating apparatus 1 and 4 described above in that light-generating apparatus 1 and 4 are each configured to be positioned within a vessel or other passage using a guidewire that extends within lumen 18 substantially throughout the apparatus. In contrast, light-generating apparatus 50 is positioned at a treatment site using a guidewire 51 that does not pass through the portion of light-generating apparatus 50 that includes the light emitting devices. Instead, guidewire 51 is disposed external to light-generating apparatus 50—at least between proximal portion 54 and distal portion 52. Thus, the part of guidewire 51 that is proximate to light emitting devices 53 is not encompassed by expandable member 57. Distal portion 52 includes an orifice 59a, and an orifice 59b. Guidewire 51 enters orifice 59a, and exits distal portion 52 through orifice 59b. It should be understood that guidewire 51 can be disposed externally to proximal portion 54, or alternatively, the proximal portion can include an opening at its proximal end through which the guidewire can enter the proximal portion, and an opening disposed proximally of light emitting devices 53, where the guidewire then exits the proximal portion.

The length of the linear light source array (i.e., light emitting devices 53 and conductive substrate 56) is only limited by the effective length of expandable member 57. If the linear array is made longer than the expandable member, light emitted from that portion of the linear array will be blocked by blood within the vessel and likely not reach the targeted tissue. As described below in connection with FIGS. 14A-14D, the use of a plurality of expandable members enables even longer linear light source arrays (i.e., longer than any single expandable member) to be used in this invention.

FIG. 6 schematically illustrates a light-generating apparatus 50a being positioned in an artery 61, to provide PDT to post PCTA lesions 60. Light-generating apparatus 50a is substantially similar to light-generating apparatus 50 described above, except for including additional light emitting devices 53a disposed in an opposed relationship with respect to light emitting devices 53, to enable light output from light-generating apparatus 50a in additional directions. Light-generating apparatus 50a thus enables lesions on opposing sides of artery 61 to be treated. In FIG. 6, light-generating apparatus 50a has been properly positioned relative to lesions 60 using radio-opaque markers 58, so as to treat the lesions with PDT (i.e., the lesions are generally disposed between the radio-opaque markers). In FIG. 7, expandable member 57 has been inflated to contact the walls of artery 61, thereby centering light-generating apparatus 50a within artery 61, and occluding blood flow through the artery, to ensure that light emitted from light emitting devices 53 and 53a reaches lesions 64 and is not blocked by blood in the artery. Guidewire 51 is removed, and the light emitting devices are energized to direct light of the required wavelengths to lesions 60, which have previously been treated with a photoreactive agent for diagnostic or therapeutic purposes. Note that it is also possible to leave the guidewire in place in the distal orifice during treatment. The wire will naturally become pressed up against the vessel wall by the expandable member (see FIG. 14C) and such an occurrence is acceptable.

FIGS. 8, 9A, and 9B are enlarged views of light source arrays that can be used in a light-generating apparatus in accord with the present invention. Light source array 80, shown in FIG. 8, includes a plurality of LEDs 86a and 86b that are coupled to a flexible, conductive substrate 82. LEDs 86a emit light of a first color, having a first wavelength, while LEDs 86b emit light of a different color, having a second wavelength. Such a configuration is useful if two different photoreactive agents have been administered, where each different photoreactive agent is activated by light of a different wavelength. Light source array 80 also includes one or more light sensing elements 84, such as photodiodes or a reference LED, similarly coupled to flexible, conductive substrate 82. Each light sensing element 84 may be coated with a wavelength-specific coating to provide a specific spectral sensitivity, and different light sensing elements can have different wavelength-specific coatings. While light source array 80 is configured linearly, with LEDs on only one side (as is the array in light-generating apparatus 50a of FIG. 5), it will be understood that different color LEDs and light sensing elements can be beneficially included in any of the light source arrays described herein.

Because the light source arrays of the present invention are intended to be used in flexible catheters inserted into blood vessels or other body passages, it is important that the light source arrays be relatively flexible, particularly where a light source array extends axially along some portion of the catheter's length. Clearly, the longer the light source array, the more flexible it must be. Light source arrays 10 and 40 (FIGS. 1A/1B, and 4A/4B, respectively) are configured in a radial orientation, and light emitted form the light sources in those arrays is directed to the distal end of the respective catheters (light-generating apparatus 1 and 4). Because light source arrays 10 and 40 do not extend axially along a substantial portion of their respective catheters, the relatively flexibility of light source arrays 10 and 40 is less important. However, light source array 80 (FIG. 8), and the light source arrays of light-generating apparatus 50 and 50a (FIGS. 5 and 6, respectively), are linearly configured arrays that extend axially along a more significant portion of their respective catheters. A required characteristic of a catheter for insertion into a blood vessel is that the catheter be sufficiently flexible to be inserted into a vessel and advanced along an often tortuous path. Thus, light source arrays that extend axially along a portion of a catheter can unduly inhibit the flexibility of that catheter. FIGS. 9A and 9B schematically illustrate axially extending light source arrays that include strain relief features that enable a more flexible linear array to be achieved.

FIG. 9A shows a linear array 88a having a plurality of light emitting sources 90 (preferably LEDS, although other types of light sources can be employed, as discussed above) mounted to both a first flexible conductive substrate 92a, and a second flexible conductive substrate 92b. Flexible conductive substrate 92b includes a plurality of strain relief features 93. Strain relief features 93 are folds in the flexible conductive substrate that enable a higher degree of flexibility to be achieved. Note that first flexible conductive substrate 92a is not specifically required and can be omitted. Further, strain relief features 93 can also be incorporated into first flexible conductive substrate 92a.

FIG. 9B shows a linear array 88b having a plurality of light emitting sources 90 mounted on a flexible conductive substrate 92c. Note that flexible conductive substrate 92c has a crenellated configuration. As shown, light emitting sources 90 are disposed in each "notch" of the crenellation. That is, light emitting sources 90 are coupled to both an upper face 93a of flexible conductive substrate 92c, and a lower face 93b of flexible conductive substrate 92c. Thus, when light emitting sources 90 are energized, light is emitted generally outwardly away from both upper surface 93a and lower surface 93b. If desired, light emitting sources 90 can be disposed on only upper surface 93a or only on lower surface 93b (i.e., light emitting sources can be disposed in every other "notch"), so that light is emitted generally outwardly away from only one of upper surface 93a and lower surface 93b. The crenellated configuration of flexible conductive substrate 92c enables a higher degree of flexibility to be achieved, because each crenellation acts as a strain relief feature.

External bond wires can increase the cross-sectional size of an LED array, and are prone to breakage when stressed. FIGS. 1A and 1B illustrate leads 10b that are exemplary of such external bond wires. FIG. 9C schematically illustrates a flip-chip mounting technique that can be used to eliminate the need for external bond wires on LEDs 94 that are mounted on upper and lower surfaces 93c and 93d (respectively) of flexible conductive substrate 92d to produce a light source array 97. Any required electrical connections 95 pass through flexible conductive substrate 92d, as opposed to extending beyond lateral sides of the flexible conductive substrate, which would tend to increase the cross-sectional area of the array. Light source array 97 is shown encapsulated in a polymer layer 23. A guidewire lumen 98a is disposed adjacent to light source array 97. An expandable balloon 99 encompasses the array and guidewire lumen. Note that either, but not both, polymer layer 23 and expandable balloon 99 can be eliminated (i.e., if the expandable balloon is used, it provides protection to the array, but if not, then the polymer layer protects the array).

FIG. 9D shows a linear array 96 including a plurality of light emitting sources (not separately shown) that spirals around a guidewire lumen 98b. Once again, balloon 99 encompasses the guidewire lumen and the array, although if no balloon is desired, a polymer layer can be used instead, as noted above. For each of the implementations described above, the array of light sources may comprise one or more LEDs, organic LEDs, super luminescent diodes, laser diodes, or light emitting polymers ranging from about 1 cm to about 10 cm in length and having a diameter of from about 1 mm to about 2 mm.

Turning now to FIG. 10, a light-generating apparatus 100 is shown as the apparatus is being positioned in a blood vessel 101, to administer PDT to treatment areas 108. Light-generating apparatus 100 is simpler in construction than light-generating apparatus 1, 4, 50, and 50a (each of which is based on a catheter), because light-generating apparatus 100 is based on a guidewire. Light-generating apparatus 100 includes a main body 102, a light source array 104, and a spring tip 106. Main body 102 is based on a conventional guidewire, preferably having a diameter ranging from about 0.10 inches to about 0.060 inches. However, main body 102 is distinguishable from a conventional guidewire because main body 102 includes electrical lead 105. Spring tip 106 is also based on a conventional guidewire spring tip. Light source array 104 includes a plurality of light emitting devices 107, each electrically coupled to lead 105 (alternatively, each light emitting device is coupled to a flexible conductive substrate, that is in turn electrically coupled to lead 105). While not separately shown, it should be understood that radio-opaque markers can be included at each end of light source array 104, thereby enabling the light source array to be properly positioned relative to treatment areas 108.

In FIG. 11, light-generating apparatus 100 has been inserted into a balloon catheter 112, and the combination of balloon catheter 112 and light-generating apparatus 100 is shown being positioned in blood vessel 101, also to administer PDT to treatment areas 108. Balloon 114 has been inflated to contact the walls of blood vessel 101, thereby centering the combination of balloon catheter 112 and light-generating apparatus 100 within blood vessel 101 and occluding blood flow that could allow blood to block light emitted from light emitting devices 107 from reaching treatment areas 108. As discussed above, the fluid used to inflate the balloon should readily transmit the wavelengths of light required to activate the photoreactive agent(s) used to treat treatment areas 108. As described above, additives can be added to the fluid to enhance light transmission and diffusion. The fluid will also act as a heat sink to absorb heat generated by light emitting devices 107, and the beneficial effect of the fluid as a coolant can be enhanced by regularly circulating the fluid through the balloon.

FIGS. 12A-12D provide details showing how light emitting devices can be integrated into guidewires. Referring to FIG. 12A, a solid guidewire 120 includes a conductive core 124 and a plurality of compartments 121 formed in the guidewire around the conductive core. Conductive core 124 is configured to be coupled to a source of electrical energy, so that electrical devices coupled to conductive core 124 can be selectively energized by current supplied by the source. Compartments 121 can be formed as divots, holes, or slots in guidewire 120, using any of a plurality of different processes, including but not limited to, machining, and laser cutting or drilling. Compartments 121 can be varied in size and shape. As illustrated, compartments 121 are arranged linearly, although such a linear configuration is not required. Preferably, each compartment 121 penetrates sufficiently deep into guidewire 120 to enable light emitting devices 122 to be placed into the compartments and be electrically coupled to the conductive core, as indicated in FIG. 12B. A conductive adhesive 123 can be beneficially employed to secure the light emitting devices into the compartments and provide the electrical connection to the conductive core. Of course, conductive adhesive 123 is not required, and any suitable electrical connections can alternatively be employed. Preferably, LEDs are employed for the light emitting devices, although as discussed above, other types of light sources can be used. If desired, only one compartment 121 can be included, although the inclusion of a plurality of compartments will enable a light source array capable of simultaneously illuminating a larger treatment area to be achieved.

Once light emitting devices 122 have been inserted into compartments 121 and electrically coupled to conductive core 124, a second electrical conductor 126, such as a flexible conductive substrate or a flexible conductive wire, is longitudinally positioned along the exterior of guidewire 120, and electrically coupled to each light emitting device 122 using suitable electrical connections 128, such as conductive adhesive 123 as (illustrated in FIG. 12B) or wire bonding (as illustrated in FIG. 12C). Guidewire 120 (and conductor 126) is then coated with an insulating layer 129, to encapsulate and insulate guidewire 120 (and conductor 126). The portion of insulating layer 129 covering light emitting devices 122 must transmit light of the wavelength(s) required to activate the photoreactive agent(s). Other portions of insulating layer 129 can block such light transmission, although it likely will be simpler to employ a homogenous insulating layer that transmits the light. Additives can be included in insulating layer 129 to enhance the distribution of light from the light emitting device, generally as described above.

With respect to guidewires including integral light sources, it should be noted that a guidewire that can emit light directly simplifies light activated therapy, because clinicians are already well versed in the use of guidewires to facilitate insertion of catheters for procedures such as angioplasty or stent delivery. A guidewire including integral light sources can be used with conventional balloon catheters, to provide a light activated therapy capability to catheters not originally exhibiting that capability. Significantly, when such a guidewire is utilized with a catheter including a central guidewire lumen and a non-compliant angioplasty balloon, inflation of the balloon will center the guidewire in the body lumen, and will hold the guidewire in place during the light therapy (so long as the balloon is inflated). The inflated balloon will exert pressure outwardly on the vessel wall and inwardly on the guidewire. Preferably, the guidewires disclosed herein with integral light sources will be similar in size, shape and handling characteristics as compared to commonly utilized conventional guidewires, such that clinicians can leverage their prior experience with non-light emitting guidewires. It is also possible to use the light emitting guidewires disclosed herein without a balloon catheter. If the vessel being treated has a diameter that is just slightly larger than the guidewire, there will be a very thin layer of blood present between the light emitting elements and the vessel wall. In this case, the light emitting guidewire can be used alone, directing the light through the thin layer of blood to treat the vessel wall. This has the advantage of allowing treatment into extremely small vessels that would otherwise not be accessible with conventional techniques.

Yet another exemplary embodiment of a guidewire incorporating light sources at a distal end of the guidewire is schematically illustrated in FIGS. 13A and 13B. A guidewire 200 is based on a nitinol hypotube 202, which includes a flexible circuit of LEDs (i.e., a light source array 220, shown in FIGS. 13B and 13F) disposed inside a distal end 204 of the hypotube. In at least one exemplary embodiment, the distal end of the nitinol hypotube is laser cut to remove a majority of the tube material proximate to the LED array, yet retain the columnar structure of the tube. In a particularly preferred embodiment, about 75-90% of the portion of the tube surrounding the LED array is eliminated. FIG. 13B enables additional details of distal end 204 of tube 202 to be identified. Note that the material removal process (e.g., laser cutting, although it should be recognized that other material removing techniques can be employed) results in the formation of a plurality of openings 206. As illustrated, the openings are generally quadrilateral in shape, although it should be recognized that the particular shape of the openings is not critical. Furthermore, it should be recognized that the dimensions noted in FIG. 13B are intended to be exemplary, rather than limiting. Openings 206 are configured to enable light from the LEDs that are disposed within the hypotube proximate to the openings to pass through the openings. Conductors 208 and 210 extend from array 220 to a proximal end of the guidewire, to enable the array to be selectively energized by an external power source.

Many conventional guidewires are available having an outer diameter of about 0.035 inches. Initial exemplary working embodiments of guidewires including integral LED light sources have ranged from about 0.0320 inches to about 0.0348 inches in diameter. Fabrication techniques are discussed in greater detail below, but in general, the LED device is potted inside the nitinol hypotube. A heat shrink tube can be applied over the openings overlying the LED array during potting/curing, to be removed afterwards, or simply left in place.

Nitinol is an excellent material for guidewires, because it exhibits sufficient flexibility and push-ability. It has radio-opaque properties, such that the LED portion will likely be readily identifiable under fluoroscopy, since the LED portion is encompassed by the plurality of openings, and the openings will reduce the radio-opacity of that portion of the guidewire relative to portions of the guidewire that do not include such openings. If necessary, additional markers can be included proximally and distally of the plurality of openings, to enable that portion of the guidewire to be precisely positioned in a body lumen. Another benefit of nitinol is that its thermal conductivity will enable heat generated by the LEDs to be more readily dissipated. Cooler operating temperatures for the LED array will improve wall plug efficiency and enable higher irradiance output. Standard steerable and anti-traumatic guidewire tips can be attached to such nitinol hypotube guidewires, distal of the light source array.

Note that guidewire 200 is configured such that a standard angioplasty catheter can fit over the entire length of guidewire 200. Thus, some sort of connector that fits inside the guidewire cross-sectional area is required, to enable the light source array disposed within the distal end of the guidewire to be electrically coupled to a power supply. In an empirical prototype, an "RCA-like" jack with two electrical terminations was fabricated from conductively-plated stainless steel capillary tubes. This connector was mated with a female connector to provide the electrical control for the LED light therapy. FIG. 13C schematically illustrates a proximal end of guidewire 200 including such a connector jack. Conductors 208 and 210 extend from the proximal end of guidewire 200 to the light source array (for example, an LED array) disposed at the distal end of guidewire 200, to enable the light source array to be energized by an external power supply (not separately shown). The connector jack includes tubes 212 and 214. When the connector jack is fully assembled, tube 214 is disposed inside tube 212, and a distal end of tube 212 is inserted into the proximal end of guidewire 200. An insulating spacer 216 separates tube 212 into a proximal portion and a distal portion. A proximal end of conductor 210 is electrically coupled to the distal portion of tube 212. Conductor 208 passes through the distal portion of tube 212, and completely through tube 214. Note that tube 214 passes through insulating spacer 216, so that conductor 208 can be electrically coupled to the proximal portion of tube 212. Any void spaces in tubes 212 and 214 are filled with an insulating potting material 218. FIG. 13D is a cross-sectional view of the connector jack taken along section line A-A of FIG. 13C, and FIG. 13E is a cross-sectional view of the connector jack taken along section line B-B of FIG. 13C. In an exemplary, but not limiting embodiment, tube 212 has an inner diameter of 0.020 inches, and an outer diameter of 0.025 inches, and tube 214 has an inner diameter of 0.012 inches, and an outer diameter of 0.018 inches.

FIG. 13F is a cross-sectional view of the distal end of guidewire 200, taken along section line C-C of FIG. 13B, enabling a light source array 220 to be observed. As noted above, void space surrounding array 220 can be filled with a potting material 218a, which is electrically insulating and optically transparent (note the potting material employed in the connector jack of FIG. 13C need not be optically transparent). In an exemplary, but not limiting embodiment, nitinol hypotube guidewire 200 has an inner diameter of 0.0270 inches (0.64 mm), and an outer diameter of 0.0325 inches (0.76 mm). Conductors 208 and 210 can be implemented, for example, using wire having an outer diameter of 0.009 inches (0.23 mm), and the light source array has a generally rectangular form factor, having maximum dimensions of 0.021 inches in width and 0.010 inches in height. It should be recognized that such stated dimensions are intended to be exemplary, rather than limiting.

FIG. 13G is a cross-sectional view of light source array 220, which includes a plurality of LEDs 224 (oriented in a linear array) mounted on a flexible non-conductive substrate 222. While no specific number of LEDs is required, empirical devices including more than 30 LEDs have been fabricated. Significantly, substrate 222 is substantially transparent to the light emitted by LEDs 224, such that light emitted from the LEDs is able to pass through the substrate. Each LED emits light from each of its six faces (the LEDs being generally cubical). Compared to two sided arrays, a single sided array offers the advantages of lower manufacturing costs, a smaller form factor, and cooler operating temperatures (resulting in a greater light output per LED). Polyimide represents an acceptable substrate material. While some polyimides have a generally yellowish tint, that tint does not substantially interfere with the transmission of red light. Empirical devices show less than a 5% transmission loss due to passage of the light through the substrate, though losses as high as 10% are still acceptable. If blue LEDs are used, higher transmission losses are to be expected, and a thinner substrate, or a different material that is more transparent to blue light, can be employed. Conductive traces 228 and bonding wires 226 enable the LEDs to be coupled to conductors 208 and 210 (not separately shown in FIG. 13G). The LEDs, traces, and bonding wires are encapsulated in potting material 218a, which as noted above, is electrically insulating and substantially optically transparent to the light emitted by the LEDs. It should be noted that the potting material need not achieve the generally rectangular form factor shown. An array including no potting material could be introduced into the distal end of the nitinol hypotube, such that the void space in the guidewire surrounding the array is filled with a potting material, thereby achieving a cylindrical rather than rectangular form factor for the potting material surrounding the array.

FIG. 13H is a plan view of array 220. Note that LEDs 224 are arranged linearly, with conductive traces 228 extending parallel to the linear array of LEDs, one trace on the right side of the LEDs, and another trace on the left side of the LEDs, with bonding wires 226 coupling the LEDs to the traces. While not specifically shown, it should be recognized that the traces are electrically coupled to the conductors 208 and 210, thereby enabling the array to be energized. In an alternative array 220a, shown in FIG. 13I, cutouts are provided in a substrate 222a underneath the LEDS, so that the flexible substrate does not interfere with the light emitted from the LED faces parallel to and immediately adjacent to the substrate (thus enabling less optically transparent substrate materials to be employed). In yet another exemplary array 220b, shown in FIG. 13J, the flexible substrate does not extend much beyond the conductive traces, such that the LED array is disposed between two parallel rails 234, each rail comprising a conductive trace deposited on top of a flexible substrate. While such a configuration is initially less structurally robust than configurations in which the supporting substrate is lager, once array 220b is encapsulated in a light transmissive potting material, such a configuration will be sufficiently robust. Significantly, array 220b is easier to manufacture than the other array designs. Each of the array configurations of FIGS. 13H, 13I, and 13J enable the LEDs to be wired in series or in parallel.

FIG. 13K is a cross-sectional view of yet another light source array 220c, which has an even smaller form factor than arrays 220, 220a, and 220b. Array 220c also includes a plurality of LEDs 224 (again oriented in a linear array) mounted on a flexible substrate 222b, with conductive traces 228a and bonding wires 226a, to enable the LEDs to be coupled to conductors configured so that the array can be energized using an external power supply (not separately shown in FIG. 13K). Note that in array 220c, the width of flexible substrate 222a is limited to the width of LEDs 224, thereby enabling a reduction in the total width to be achieved. The positions of bonding wires 226a are changed relative to their orientation in arrays 220, 220a, and 220b. This change is clearly illustrated in FIG. 13L, which shows a plan view of array 220c. Note that traces 228a are oriented perpendicular to an axis 230 along which the linear LED array extends. Significantly, the LEDs in array 220c can only be wired in series.

FIG. 13M schematically illustrates how array 220c can be manufactured. A plurality of LEDs 224 and traces 228b are deposited onto an extensive substrate 222c. Bonding wires 226a are used to electrically couple the LEDs to the traces. The substrate is cut as indicated by arrows 232, thereby creating three linear arrays 220c. It should be recognized that each linear array 220c can include more than two LEDs.

FIG. 13N is a schematic view of a guidewire 200a, enabling details of distal end 204 of tube 202a to be identified. Guidewire 200a is smaller in diameter than guidewire 200, enabling the narrower linear light source array (i.e., array 220c) to be employed. In addition to the plurality of openings 206, guidewire 200a includes an opening 236 disposed distally of openings 206, encompassing array 220c. Because the potting material encompassing array 220a doesn't need to extend proximally of the array, the portion of tube 202a extending proximally of array 220c defines a substantial lumen that can be used to deliver a fluid, such as a drug, to opening 236. In one exemplary embodiment, natural blood flow in a body lumen will carry the drug downstream toward the vessel wall that would be illuminated by the LEDs in array 220c. Yet another structure that can be used to deliver such a drug comprises an optional compliant balloon 238 with micro-pores configured to leak the drug into the body lumen once a certain pressure is reached, while the compliant balloon conforms to the body lumen. If such a balloon is used, opening 236 is not required, and the fluid entering the balloon is provided by the hollow tube proximal of the array.

FIG. 13O is a cross-sectional view of a distal end of guidewire 200a, taken along section line D-D of FIG. 13N, into which array 220c has been inserted. Any void space surrounding array 220c can be filled with potting material 218a, which is electrically insulating and optically transparent. In an exemplary, but not limiting embodiment, nitinol hypotube guidewire 200a has an inner diameter of 0.0170 inches, and an outer diameter of 0.0204 inches. Significantly, guidewire 200a is implemented in this embodiment using silver-coated nitinol, such that the guidewire itself can be used as one of the paired conductors required to energize array 220a. The silver coating is deposited on the interior surface of the hypotube, forming a reflective interior that enhances light emission from the LED array. It should be noted however, that the conductive coating can also be applied to the external surface of the guidewire. While a silver coating is preferred, other conductive coatings (e.g., gold, copper, and/or other conductive elements or alloys) can be employed. Because the guidewire includes a conductive coating, only a single conductor 234 is required to be disposed within guidewire 200a. Conductor 234 is implemented using 36 gauge wire (AWG) for conveying a positive signal, while the silver-coated nitinol hypotube conveys a ground signal. As noted above, light source array 220a has a generally rectangular form factor, having maximum dimensions of 0.015 inches in width and 0.009 inches in height. Again, it should be recognized that such stated dimensions are intended to be exemplary, rather than limiting. While nitinol represents an exemplary material, it should be recognized that many other materials, such as polymers and other metals (such stainless steel, to mention just one additional example), can be employed to implement a hollow guidewire.

FIG. 13P is a cross-sectional view of guidewire 200a, taken along section line E-E of FIG. 13N. Note that open lumen 235 surrounding conductor 234 can be used as a fluid delivery lumen.

With respect to the LEDs employed in the arrays, non-reflector LED semiconductors that emit light out all six sides can be employed. These LED dies can be attached to a polyimide flexible substrate without traces under the LED dies, such that light is projected through the polyimide material. In the visible red region the polyimide can pass over 90% of the light. If a slightly less standard polyester flex circuit is used then the entire visible spectrum down into UV ranges pass well over 95% of the emitted light.

Groups of LEDs can be connected in series in order to average the forward voltage drop variation of individual dies; as this technique greatly improves manufacturing consistency. If longer lightbars/arrays are required, then such serial grouping can be connected in parallel. For example, in one empirical exemplary embodiment, eight parallel groups of six LEDs connected in series (i.e., 48 LEDs) were used to fabricate a linear array 5 cm in length.

With respect to embodiments including a plurality of expandable members, such a configuration enables a linear light source array that is longer than any one expandable member to be employed to illuminate a treatment area that is also longer than any one expandable member. FIGS. 14A, 14B, 14C, and 14D illustrate apparatus including such a plurality of expandable members. FIGS. 14A and 14B show an apparatus employed in connection with an illuminated guidewire, while FIGS. 14C and 14D illustrate an apparatus that includes a linear light source array combined with the plurality of expandable members. In each embodiment shown in these FIGURES, a relatively long light source array (i.e., a light source array having a length greater than a length of any expandable member) is disposed between a most proximally positioned expandable member and a most distally positioned expandable member.

FIG. 14A schematically illustrates a light-generating apparatus 131 for treating relatively long lesions (i.e., lesions of about of 60 mm in length or longer) in a blood vessel 137. Light-generating apparatus 131 is based on a multi-lumen catheter 130 in combination with an illuminated guidewire 135 having integral light emitting devices. Multi-lumen catheter 130 is elongate and flexible, and includes a plurality of expandable members 133a-133d. While four such expandable members are shown, alternatively, more or fewer expandable members can be employed, with at least two expandable members being particularly preferred. As discussed above, such expandable members occlude blood flow and center the catheter in the vessel. Multi-lumen catheter 130 and expandable members 133a-133d preferably are formed from a suitable bio-compatible polymer, including but not limited to: polyurethane, polyethylene, PEP, PTFE, PET, PEBA, PEBAX or nylon. Each expandable member 133a-133d preferably ranges from about 2 mm to about 15 mm in diameter and from about 1 mm to about 60 mm in length. When inflated, expandable members 133a-133d are pressurized from about 0.1 atmosphere to about 16 atmospheres. It should be understood that between expandable member 133a and expandable member 133d, multi-lumen catheter 130 is formed of a flexible material that readily transmits light of the wavelengths required to activate the photoreactive agent(s) with which light-generating apparatus 131 will be used. Bio-compatible polymers having the required optical characteristics can be beneficially employed. As discussed above, additives such as diffusion agents can be added to the polymer to enhance the transmission or diffusion of light. Of course, all of multi-lumen catheter 130 can be formed of the same material, rather than just the portions between expandable member 133a and expandable member 133d. Preferably, each expandable member 133a-133d is similarly constructed of a material that will transmit light having the required wavelength(s). Further, any fluid used to inflate the expandable members should similarly transmit light having the required wavelength(s).

Referring to the cross-sectional view of FIG. 14B (taken along lines section lines A-A of FIG. 14A), it will be apparent that multi-lumen catheter 130 includes an inflation lumen 132a in fluid communication with expandable member 133a, a second inflation lumen 132b in fluid communication with expandable members 133b-c, a flushing lumen 134, and a working lumen 136. If desired, each expandable member can be placed in fluid communication with an individual inflation lumen. Multi-lumen catheter 130 is configured such that flushing lumen 134 is in fluid communication with at least one port 138 (see FIG. 14A) formed through the wall of multi-lumen catheter 130. As illustrated, a single port 138 is disposed between expandable member 133a and expandable member 133b and functions as explained below.

Once multi-lumen catheter 130 is positioned within blood vessel 137 so that a target area is disposed between expandable member 133a and expandable member 133d, inflation lumen 132a is first used to inflate expandable member 133a. Then, the flushing fluid is introduced into blood vessel 137 through port 138. The flushing fluid displaces blood distal to expandable member 133a. After sufficient flushing fluid has displaced the blood flow, inflation lumen 132b is used to inflate expandable members 133b, 133c, thereby trapping the flushing fluid in portions 137a, 137b, and 137c of blood vessel 137. The flushing fluid readily transmits light of the wavelength(s) used in administering PDT, whereas if blood were disposed in portions 137a, 137b, and 137c of blood vessel 137, light transmission would be blocked. An alternative configuration would be to provide an inflation lumen for each expandable member, and a flushing port disposed between each expandable member. The expandable members can then be inflated, and each distal region can be flushed, in a sequential fashion.

A preferred flushing fluid is saline. Other flushing fluids can be used, so long as they are non toxic and readily transmit light of the required wavelength(s). As discussed above, additives can be included in flushing fluids to enhance light transmission and dispersion relative to the target tissue. Working lumen 136 is sized to accommodate light emitting guidewire 135, which can be fabricated as described above. Multi-lumen catheter 130 can be positioned using a conventional guidewire that does not include light emitting devices. Once multi-lumen catheter 130 is properly positioned and the expandable members are inflated, the conventional guidewire is removed and replaced with a light emitting device, such as an optical fiber coupled to an external source, or a linear array of light emitting devices, such as LEDs coupled to a flexible conductive substrate. While not specifically shown, it will be understood that radio-opaque markers such as those discussed above can be beneficially incorporated into light-generating apparatus 131 to enable expandable members 133a and 133d to be properly positioned relative to the target tissue.

Still another embodiment of the present invention is light-generating apparatus 141, which is shown in FIG. 14C disposed in a blood vessel 147. Light-generating apparatus 141 is similar to light-generating apparatus 131 describe above, and further includes openings for using an external guide wire, as described above in connection with FIG. 5. An additional difference between this embodiment and light-generating apparatus 131 is that where light emitting devices were not incorporated into multi-lumen catheter 130 of light-generating apparatus 131, a light emitting array 146 is incorporated into the catheter portion of light-generating apparatus 141. FIGS. 1, 2, and 5 show exemplary configurations for incorporating light emitting devices into a catheter.

Light-generating apparatus 141 is based on an elongate and flexible multi-lumen catheter 140 that includes light emitting array 146 and a plurality of expandable members 142a-142d. Light emitting array 146 preferably comprises a linear array of LEDs. As noted above, while four expandable members are shown, more or fewer expandable members can be employed, with at least two expandable members being particularly preferred. The materials and sizes of expandable members 142a-142d are preferably consistent with those described above in conjunction with multi-lumen catheter 130. The walls of multi-lumen catheter 140 proximate to light emitting array 146 are formed of a flexible material that does not substantially reduce the transmission of light of the wavelengths required to activate the photoreactive agent(s) with which light-generating apparatus 141 will be used. As indicated above, bio-compatible polymers having the required optical characteristics can be beneficially employed, and appropriate additives can be used. Preferably, each expandable member is constructed of a material and inflated using a fluid that readily transmit light of the required wavelength(s).

Referring to the cross-sectional view of FIG. 14D (taken along section line B-B of FIG. 14C), it can be seen that multi-lumen catheter 140 includes an inflation lumen 143a in fluid communication with expandable member 142a, a second inflation lumen 143b in fluid communication with expandable members 142b-c, a flushing lumen 144, and a working lumen 149. Again, if desired, each expandable member can be placed in fluid communication with an individual inflation lumen. Multi-lumen catheter 140 is configured so that flushing lumen 144 is in fluid communication with a port 148 (see FIG. 14C) formed in the wall of multi-lumen catheter 140, which enables a flushing fluid to be introduced into portions 147a-147c of blood vessel 147 (i.e., into those portions distal of expandable member 142a). Those portions are isolated using inflation lumen 143b to inflate expandable members 142*b*-142*d*. The flushing fluid is selected as described above. Working lumen 149 is sized to accommodate light emitting array 146. Electrical leads 146*b* within working lumen 149 are configured to couple to an external power supply, thereby enabling the light source array to be selectively energized with an electrical current. A distal end 139 of multi-lumen catheter 140 includes an opening 160*a* in the catheter side wall configured to enable guidewire 145 (disposed outside of multi-lumen catheter 140) to enter a lumen (not shown) in the distal end of the catheter that extends between opening 160*a* and an opening 160*b*, thereby enabling multi-lumen catheter 140 to be advanced over guidewire 145. Note that it is also possible to create this device with a single lumen extrusion. For example, the LED array and connection wires could share the lumen with the inflation fluid. Each expandable member would also be in contact with this lumen through inflation ports cut into the extrusion. When the flushing fluid is provided it serves multiple functions—1) it cools the LEDs directly, 2) it provides good optical coupling between the LEDs and the outside of the catheter, and 3) it inflates the expandable members (all at the same time). This is a simpler version of the design, which does not require a multi-lumen catheter.

FIG. 15 shows an alternative embodiment of the light-generating apparatus illustrated in FIGS. 14A, 14B, 14C, and 14D. A light-generating apparatus 150 in FIG. 15 is based on a multi-lumen catheter having an elongate, flexible body 154 formed from a suitable bio-compatible polymer and expandable members 152*a*-152*d*. As indicated above, at least two expandable members are particularly preferred. The difference between light-generating apparatus 150 and light-generating apparatus 131 and 141, which were discussed above, is that the expandable members in light-generating apparatus 150 are fabricated as integral portions of body 154, while the expandable members of light-generating apparatus 131 and 141 are preferably implemented as separate elements attached to a separate catheter body.

Yet another exemplary embodiment of a light generating catheter disclosed herein is configured to be used with an introducer catheter having a single lumen. A distal end of such a light generating catheter includes a linear light source array. This concept is schematically illustrated in FIG. 16A. This exemplary embodiment has been designed to be used with an introducer catheter 240 having an inner diameter of 0.65 inches (1.65 mm) and an outer diameter of 0.050 inches (1.27 mm). It should be recognized however, that the dimensions disclosed herein are intended to be exemplary, and not limiting. A conventional guidewire 244 (i.e., not a light emitting guidewire, as discussed above) is disposed within a central lumen 242, in introducer catheter 240. In an exemplary embodiment, guidewire 244 has an outer diameter of 0.014 inches (0.36 mm). A light emitting catheter 246 is also disposed within central lumen 242. A flexible light source array 248 is disposed in a distal end light emitting catheter 246. FIG. 16B provides additional details relating to array 248, which is generally similar to array 220 of FIG. 13G, except for the use of a slightly thicker flexible substrate 222*d*. Preferred dimensions for array 248 are a maximum width of 0.028 inches and a maximum height of 0.013 inches.

Referring once again to FIG. 16A, note that a push wire 250 is disposed under array 248. Significantly, push wire 250 serves as a heat sink to enable heat from the LEDs in array 248 to be dissipated, significantly increasing the efficiency of the array (as measured by the amount of light output per LED—noting that cooler LEDs emit higher intensity light). Array 248 and push wire 250 are encapsulated in optically transparent potting material 218*a* (it should be apparent that the potting material need not be transparent to all wavelengths, but should at least be transparent to the wavelengths emitted by the light sources in array 248). The potting material need not extend the entire length of light emitting catheter 246. Instead, the potting compound need only be disposed at the distal end of light emitting catheter 246, such that array 248 is encapsulated. Thus, only a distal end of push wire 250 need be encapsulated in the potting compound. Note also that potting material 218*a* does not fill the entire interior of the distal end of light emitting catheter 246. As a result, an annular lumen 252 is defined between the inner diameter of the light emitting catheter and the potting material encapsulating array 248. Annular lumen 252 has a volume of at least 0.000177 cubic inches, so that if the distal end of light emitting catheter 246 is advanced distally of a distal end of introducer catheter 240, a balloon can be incorporated into the distal end of light emitting catheter to surround the light source array (generally as discussed above), and annular lumen 252 will be sufficiently large to service such a balloon. Proximally of array 248, annular lumen 252 significantly increases in size, since the only elements disposed in the lumen will be push wire 250 and the electrical conductors used to energize the array. The lumen in light emitting catheter 246 will be filled with a column of fluid.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A light emitting guidewire comprising:
   a flexible integrated guidewire, comprising;
      a hollow tube, having a proximal and a distal end;
      a first conductive path disposed within the hollow tube from the proximal to the distal end comprising a first wire; and
      a second conductive path disposed within the hollow tube from the proximal to the distal end and comprising a second wire;
   a plurality of light sources disposed at the distal end of the tube; and
   an external power supply energizing the plurality of light sources;
   wherein the first and the second conductive paths are configured to electrically couple the plurality of light sources to the external power supply and supply illuminating power to the plurality of light sources, and
   wherein at least one of the first and the second conductive paths comprises a crenellated configuration.

2. The light emitting guidewire of claim 1, wherein the guidewire comprises at least one compartment formed into the distal end of the guidewire, the at least one compartment being sized and shaped to accommodate the plurality of light sources.

3. The light emitting guidewire of claim 2, wherein the at least one compartment comprises a plurality of compartments, such that each different light source is disposed in a corresponding different compartment.

4. The light emitting guidewire of claim 3, wherein the plurality of compartments are configured to function as a strain relief feature, to enhance a flexibility of the guidewire.

5. The light emitting guidewire of claim 1, wherein the hollow tube further comprises a plurality of openings disposed proximate to the distal end of the tube, and
wherein the plurality of light sources comprises a light source array disposed within the hollow tube, such that the plurality of openings encompass the array.

6. The light emitting guidewire of claim 5, wherein the array is encapsulated in a potting material that is electrically insulating and optically transparent to the light emitted by the array.

7. The light emitting guidewire of claim 1, further comprising a plurality of compartments formed into the distal end of the guidewire, each compartment being sized and shaped to accommodate at least one light source in a light source array at the distal end.

8. The light emitting guidewire of claim 7, wherein the plurality of compartments are configured linearly.

9. The light emitting guidewire of claim 1, further comprising an electrical lead and an insulating layer, the electrical lead defining at least one of the conductive paths, and the insulating layer is configured to encapsulate and insulate the electrical lead.

10. The light emitting guidewire of claim 9, wherein the insulating layer comprises a portion covering at least one light source, the portion being configured to transmit light emitted by the plurality of light sources.

11. The light emitting guidewire of claim 9, wherein the insulating layer comprise additives configured to enhance a distribution of light from the plurality of light sources.

* * * * *

UNITED STATES PATENT AND TRADEMARK OFFICE
CERTIFICATE OF CORRECTION

PATENT NO. : 10,376,711 B2  
APPLICATION NO. : 11/834572  
DATED : August 13, 2019  
INVENTOR(S) : Phillip Burwell et al.

Page 1 of 1

It is certified that error appears in the above-identified patent and that said Letters Patent is hereby corrected as shown below:

On the Title Page

Item (75) add:
William Barnard, Maple Valley, WA (US)

Signed and Sealed this
First Day of October, 2019

Andrei Iancu
*Director of the United States Patent and Trademark Office*